United States Patent [19]
Donaldson

[11] Patent Number: 5,162,306
[45] Date of Patent: * Nov. 10, 1992

[54] COMPOSITION AND METHOD FOR PRODUCING SUPEROVULATION IN MAMMALS

[76] Inventor: Lloyd E. Donaldson, Rt. 8, Box 324-12, Tyler, Tex. 75703

[*] Notice: The portion of the term of this patent subsequent to Oct. 25, 2005 has been disclaimed.

[21] Appl. No.: 668,809

[22] Filed: Mar. 8, 1991

Related U.S. Application Data

[63] Continuation of Ser. No. 255,041, Oct. 7, 1988, abandoned, which is a continuation-in-part of Ser. No. 6,372, Jan. 23, 1987, Pat. No. 4,780,451.

[51] Int. Cl.$^5$ .............................................. A61K 37/38
[52] U.S. Cl. ........................................ 514/12; 514/15; 514/14; 514/2; 514/800; 530/313
[58] Field of Search ..................... 514/12, 14, 2, 800, 514/15; 530/313, 328; 930/130

[56] References Cited

U.S. PATENT DOCUMENTS 4,670,419  6/1987  Uda et al. .............................. 514/16

OTHER PUBLICATIONS

Science, vol. 211, 23 Jan. 1981, pp. 351–358, Seidel, Jr.
Biotechnology, 1984, pp. 149–160, Mapletoft Theriogenology, vol. 25, No. 6, 1986, Donaldson et al.
The Veterinary Record, Dec. 1986, Donaldson et al.
Chem. Abs., vol. 91, 1979, 703k.
Chem. Abs., vol. 100, 1984, 96979h.
Chem. Abs., vol. 100, 1984, 168613j.
D. T. Armstrong & G. Evans, *Factors Influencing Success of Embryo Transfer in Sheep and Goats*, Theriogenology, Jan. 1983, vol. 19.
Kiessling et al., *Superovulation and Embryo Transfer in the Dairy Goat*, JAVMA, vol. 188, No. 8, Apr. 15, 1986, pp. 829–832.
Armstrong et al., *Superovulation Treatments and Embryo Transfer in Agora Goats*, J. Reprod. Fert. (1983) 67, 403–410.
Manuscript copy of *Biosynthesis and Secretion of Follicle Stimulating Hormone* by Chappel et al., published in Endocrine Reviews 4 (2) 179–211 (1987).

*Primary Examiner*—Merrell C. Cashion, Jr.
*Assistant Examiner*—T. D. Wessendorf
*Attorney, Agent, or Firm*—Hubbard, Thurman, Tucker & Harris

[57] ABSTRACT

A hormone composition for producing superovulation in mammals. The composition has a particular ratio of follicle stimulating hormone (FSH) and luteinizing hormone (LH) which produces an optimum ovulation response in mammals and promotes out of season breeding and twinning. The composition can be produced from mammal pituitary glands or by recombinant DNA procedures and can be preserved in a phosphate buffered saline solution of thymol.

13 Claims, 4 Drawing Sheets

COMPOSITION AND METHOD FOR PRODUCING SUPEROVULATION IN MAMMALS

This application is a continuation of application Ser. No. 255,041, filed Oct. 7, 1988 now abandoned, which is a continuation-in-part application, Ser. No. 006,372, filed Jan. 23, 1987, now U.S. Pat. No. 4,780,451.

BACKGROUND OF THE INVENTION

1. Field of the Invention

The present invention relates to a composition and method for producing an optimum ovulation response in mammals.

2. Description of the Prior Art

In mammals, the fetal or neonatal female produces thousands of oocytes, most of which are never ovulated and most of those ovulated are never fertilized. A multimillion dollar industry has developed that is concerned with methods to ovulate, fertilize and utilize these embryos either in the mother or by transfer of these oocytes to surrogate mothers. The advantages of such procedures include increasing the reproductive rate of valuable mammals, by decreasing the generation interval; enabling the progeny testing of females, the use of superior females as donors, and increasing the number of progeny per female through controlled multiple births, and transporting embryos with selected genetic characteristics to distant places.

It is also possible and especially desirable to stimulate the production of ova at each estrus, effectively multiplying the reproductive capacity of the mammal. The introduction of multiple follicle growth with subsequent ovulation is referred to as "superovulation" and promotes out of season breeding and twinning. For example, it is an established commercial practice to stimulate the formation of multiple ovarian follicles in cattle and other domestic animals by multiple injections of follicle stimulation hormone.

It is an established commercial practice to stimulate estrus and ovulation in sheep, rabbits and other mammals at a time other than their normal breeding season or period. It is also a commercial husbandry practice to induce twinning in cattle and increase the numbers of offspring in sheep, pigs, and other species.

The all important first step in these procedures is to produce a superovulation response in a superior female donor. The objective of superovulation is to increase the number of normal fertile eggs or embryos per donor. The basic principle of superovulation is to stimulate extensive follicular development through intramuscular or subcutaneous administration of a preparation having follicle-stimulating hormone (FSH) activity at levels in excess of normal endogenous levels. The most commonly used sources for this preparation are swine pituitary extracts or pregnant mares' serum. The gonadotropic hormones have become known as follicle-stimulating hormone (FSH) and luteinizing hormone (LH) based on their effects on ovarian follicular activity. The activity of FSH and LH preparations are usually measured by bioassay and compared to a reference standard. Typical reference standards are the National Institute of Health standards which are designated NIH-FSH-S1 and NIH-LH-S1 for FSH and LH respectively. The S1 refers to the NIH standard #1.

Treatment of mammals, for example, cattle, horses, rabbits and many exotic (wild) species with gonadotropins leads to ovulation of numerous ova instead of the usual one. In cattle, gonadotropin treatment is usually initiated between days 9 and 14 of the estrus cycle (estrus is day 0), causing ovarian follicles to grow. Two or three days after the start of treatment, prostaglandin $F_{2\alpha}$ or an analog is injected to terminate the luteal phase of the estrus cycle prematurely by lysing the corpus luteum; about 2 days later estrus occurs. Estrus lasts about 12 to 18 hours and ovulation occurs about 28 hours after the onset of estrus, and fertilization probably occurs a few hours after ovulation.

Before prostaglandins became available, superovulation was initiated about 4 to 5 days before the end of the estrus cycle, a time that could not be estimated accurately. Availability of prostaglandin $F_{2\alpha}$ has improved the efficacy of superovulation and has also provided flexibility in scheduling donors.

Because the best bulls are usually propagated only with frozen semen, artificial insemination is used routinely for valuable cows. Sometimes mixtures of semen from two or three bulls are used with superovulation, and the progeny are sorted out after birth on the basis of blood type.

Bovine embryos usually move from the oviduct to the uterus 72 hours after the onset of estrus, although in superovulated cows a few remain in the oviduct through day 7. A high percentage of embryos can usually be recovered nonsurgically from the uterus six or seven days after the beginning of estrus. Recovery of embryos from the oviduct requires surgery and, therefore, is recommended only in certain cases of infertility.

To recover embryos, a Foley catheter is inserted through the cervix into the uterus by palpating through the wall of the rectum with one hand as is done for artificial insemination. The latex catheter consists of three channels for inflow, outflow, and inflation of a balloon-like cuff that prevents the escape of fluid after insertion. Each uterine horn is filled and emptied five to ten times with 30 to 200 milliliters of fluid each time, according to the size of the uterus. The embryos are flushed out with this fluid into large graduated cylinders. Embryos can be filtered or allowed to settle for 30 minutes and can then be located under a stereomicroscope by searching through an aliquot from the bottom of the cylinder. They are then stored in small containers until transfer.

Embryos and ova from the one-cell to the early blastocyst stage (7 to 8 days after estrus) are between 120 and 140 micrometers in diameter exclusive of the zona pellucida. Between days 8 and 10, they double in diameter, hatch from the zona pellucida, and then grow to 20 centimeters or more in length by day 18. Since bovine embryos form no intimate attachment to the uterus before day 18, they can be recovered nonsurgically until this time, although they are increasingly prone to damage after day 14. It appears that a larger number of normal embryos can be obtained non-surgically 6 to 8 days after estrus than at other times.

It has been shown (Donaldson et al., Theriogenology 23, 189 (1985); Donaldson et al., Theriogenology 25, 749 (1986)), that luteinizing hormone (LH) contamination of follicle stimulating hormone (FSH) reduces the superovulation response in cattle. The excessive variability in superovulation response in cattle to a standardized quantity of FSH was reported in 1944 (Hammond et al., Journal Agricultural Science 34, 1 (1944)), but it was not until forty years later when the dynamics of follicular development and the response to exogenous gonadotropins was described (Monneaux et al., Theriogenology 19, 55 (1983); Moor et al., Theriogenology 21, 103 (1984)) that more reliable superovulation techniques began to be developed. It has been shown that commercial FSH preparations have high and variable LH contents (Murphy et al., Theriogenology 21, 117 (1984); Lindsell et al., Theriogenology 25, 167 (1986)). Excess LH in a superovulatory hormone has been shown to cause premature stimulation of the oocyte (Moor et al. Theriogenology 21, 103 (1984)). Rat oocytes produced by superovulation have been shown to exhibit reduced fertilization rates (Walton et al., Journal of Reproduction and Fertility 67, 91 (1983); Walton et al., Journal of Reproduction and Fertility 67,309 (1983)). Low fertilization rates in superovulated cattle have been shown not to have resulted from the quantity of semen used or the number of times the cow was bred (Donaldson, Veterinary Record 117, 35 (1985)).

It has been shown that normal preovulatory progesterone (P4) LH and FSH concentrations are necessary for optimal embryo production from superovulated cows (Donaldson, Theriogenology 23, 441 (1985); Calleson et al., Theriogenology 25, 71 (1986)). Abnormal concentrations of P4, LH and FSH are followed by abnormal follicular/oocyte maturation and lowered embryo production.

A commonly available FSH preparation manufactured by Armour Pharmaceutical Co. and known as FSH-P is a crude pituitary extract having a high and variable LH content. The LH content has been measured and the FSH/LH ratio has been found to be less than 100. Armour Pharmaceutical Co. is the assignee of U.S. Pat. Nos. 2,799,621 and 3,119,740 which relate to the preparation of FSH-P.

U.S. Pat. No. 2,799,621 to Steelman is directed to a method for recovering both adrenocorticotropin (ACTH) and gonadotropins (FSH and LH) from the same batch of pituitary material.

U.S. Pat. No. 3,119,740 to Steelman, et al. is directed to a method for preparing follicle stimulating hormone (FSH) free from contaminant physiological factors.

Development of reliable superovulation methods in cattle for producing adequate and predictable numbers of embryos has been slow (Moor et al., Theriogenology 21:103-116 (1984)). As noted above, the excessive variability in the numbers of ova shed in response to a standardized amount of injected hormone was first reported in 1944 (Hammond et al., Journal Agricultural Science 34, 1 (1944)), but it was not until 1983 (Monneaux et al., Theriogenology 19, 55 (1983); Moor et al., Theriogenology 21:103-116 (1984)) that the reasons for this variability began to be understood. The dynamics of follicular development during the bovine estrus cycle, the response to exogenous gonadotropins (Moor et al., Theriogenology 19, 55 (1983); Moor et al., Theriogenology 21:103-116 (1984)), and the differences in the relative abundance of FSH and LH activity in gonadotropin preparations (Murphy et al., Theriogenology 21:117-125 (1984)) contribute to this variability. The ratio of FSH to LH activity in the various hormone preparations used for superovulation varies between batches of Armour's FSH-P and between FSH-P and pregnant mare serum gonadotropin (PMSG) (Monneaux et al., Theriogenology 19:55-64 (1983); Murphy et al., Theriogenology 22:205-212 (1984)). FSH stimulates the growth of granulosa cells in preantral and small antral follicles (Monneaux et al., Theriogenology 19:55-64 (1983)) and reverses the process of atresia in follicles over 1.7 mm in diameter (Moor et al., Theriogenology 21:103-116 (1984)). The LH surge is responsible for the resumption of meiosis in the preovulatory oocyte, and the reduction in the high LH content of pituitary gonadotropin preparations should decrease premature activation of oocytes during superovulation (Moor et al., Theriogenology 21:103-116 (1984)). A previous study (Donaldson, Theriogenology 22:205-212 (1984)) showed that embryo production depended upon the dose of FSH-P. As the dose increased above an optimal 28 mg, three embryo production endpoints declined: the number of transferable embryos, the total embryos recovered, and the percent transferable. The number of collections at which no embryos were recovered also increased.

Considering the potential immunological reactions that might be encountered, employing bovine preparations in treatments involving cattle seems appropriate. The purification of bovine FSH has been reported (Beckers et al., Biochemie 59:825-831 (1977); Cheng, Biochem. J. 159:651-659 (1976); Grimek et al. Endocrinology 104:140-147 (1979)). However, the content of FSH in bovine pituituaries is relatively low and the recovery with purification is generally poor. Porcine pituitaries are as readily available and the FSH content seems more amenable to extraction and processing. Indeed, commercially available preparations of porcine origin have been widely used in veterinary medicine. Methods for the purification of porcine FSH have also been described (Closset et al., Eur. J. Biochem. 86:105-113 (1978); Whitley et al., Endocrinology 102:1874-1886 (1978)). The amino acid sequence for porcine FSH has been proposed (Closet., Eur J. Biochem. 86:115-120 (1978)), but there is no reported sequence for the bovine hormone.

It has been shown how LH is needed in all mammals to act on follicular cells to produce estrogen in developing follicle, i.e., a prerequisite to stimulation by FSH in superovulation (JoAnne S. Richards, *Physiological Review*, Vol. 60, No. 1, January 1980, pp. 51-89). The Richards publication directed investigators to consider adding LH to available FSH in order to try to improve superovulation. In the mammal species, including goats, sheep, and laboratory animals, it was reported that same problem regarding superovulated mammals with FSH and PMSG (pregnant mare serum gonadotrophin) resulted as was reported in the cattle species, i.e., fertilization failure and degeneration of embryos. The investigators reported "FSH-P was found more consistently to result in increased ovulation rate with a lower incident of excess large follicles which failed to ovulate than PMSG". The investigators did not realize that this enhanced results with FSH-P was due to the LH content and effect. (D. T. Armstrong, et al, Theriogenology, January, 1983, Vol. 19, No. 1, pp. 30-42). Continuing investigations determined that studies of the effectiveness of FSH-P, when administered at an approximate dose in combination with progestagen to induce estrus and fertile mating in seasonally anestrous ewes; however, no advantage over PMSG was evident and a major disadvantage of the FSH was the need to administer the FSH in multiple doses because of its short half-life (D. T. Armstrong, et al, Proc. 10th International Congress Animal Reproduction ART. INSEM., Urbana, Ill., USA, June 10-14, 1984, pp. VII-VIII-VII-XV).

In 1983, a paper entitled *Factors Regulating Growth of Preovulatory Follicle in the Sheep and Human* was presented by D. T. Baird and published in Journal Reproduction and Fertilization (1983), 69, 343-352, the similarity between sheep and humans in relying on LH and FSH to cause growth in follicles was presented. Further investigation by Scott C. Chappel, et al, published in Endocrine Reviews 4[2] 179-211 (1987) concluded that early follicular phase requires FSH and LH, with LH causing production of androgenic steroids and FSH utilizing these steroids and connects these steroids to estrogens. Follicle growth as a result of local estrogen and FSH stimulation is a result. It would appear from these and other papers that enhancement of ovulation requires some LH in the beginning and FSH to continue the process in all mammals.

Earlier investigations established that follicular development (growth) is fundamentally the same in all mammalian species. Investigators are interested in the growth of preantral follicles and this requires LH to cause the production of estrogens which, with FSH, cause follicles to grow (Scott C. Chappel, et al and JoAnne S. Richards). These earlier investigations, recognizing the need for LH resulted in many investigators adding LH to available FSH which had LH present as unknown contamination, thus resulting in confusing as well as conflicting data.

SUMMARY OF THE INVENTION

The present invention is directed to a hormone ovulation and composition for producing superovulation in mammals that avoids the above-mentioned disadvantages which are characteristic of the prior art. More specifically, the present invention is directed to a hormone composition comprising a particular ratio of follicle stimulating hormone (FSH) and luteinizing hormone (LH) which produces an optimum superovulation response in mammals. The hormone composition of the present invention can be produced from animal pituitary glands or by recombinant DNA procedures and can be preserved in saline or phosphate buffered saline solutions of thymol (5-methyl-2methylethyl)phenol.

The hormone composition of the present invention, preferably, has a FSH to LH ratio of from about 500 to about 30,000. Most preferably, the pituitary hormone composition of the present invention has a FSH to LH ratio of from about 1000 to about 23,000. These ratios were determined according to National Institute of Health standards designated as NIH-FSH-S1 and NIH-LH-S1 for FSH and LH respectively, the S1 referring to NIH standard #1.

On a molecular basis, since the molecular weights of FSH and LH are essentially the same, the FSH/LH ratios can be presented in the context of effective units per volume. Pure FSH assays at 120 NIH-FSH-S1 units per milligram. Pure LH assays at 1.5 NIH-LH-S1 units per milligram. Thus 1 LH unit has 80 times more activity than 1 unit FSH. Since the molecular weights of FSH and LH are essentially the same these units can be converted to a molecular (weight) basis. FSH/LH ratios can be converted to percent LH content by the ratio 8000/(FSH/LH ratio). Thus a pro duct with an FSH/LH ratio of 30,000 contains 0.26% of LH and one with a ratio of 500 contains 16% LH. FSH-P with a ratio >100 contains more than 80% LH.

A preferred embodiment of the invention presents a composition of matter for producing superovulation in mammals comprising an effective amount of follicle stimulation hormone and luteinizing hormone, wherein the ratio of follicle stimulation hormone to luteinizing hormone is in a range of from about 500 to about 30,000 to 1.

The present invention is also directed to a method for producing superovulation, out of season breeding and twinning in mammals. The method of the present invention comprises administering to cattle, sheep, goats, domestic and exotic mammals, the composition of the present invention.

BRIEF DESCRIPTION OF THE DRAWINGS

FIGS. 2 and 3 are related since they were prepared using the same batch, with FIG. 2 illustrating the batch with 0.1% by weight Thymol preservative and FIG. 3 illustrating the batch without Thymol preservative added.

FIGS. 4 and 5 illustrate a different batch with FIG. 4 having 0.1% Thymol preservative added and FIG. 5 without any Thymol preservative addition.

FIGS. 6 and 7 present yet another batch with FIG. 6 including 0.1% by weight Thymol preservative and FIG. 7 presenting data without the preservative addition.

DETAILED DESCRIPTION OF THE PREFERRED EMBODIMENTS

Figure 1:
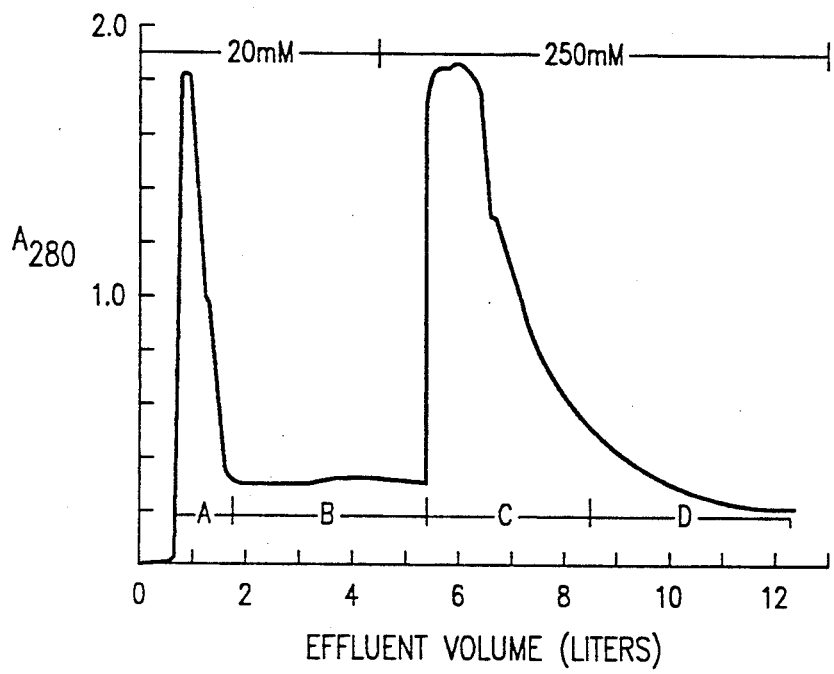
FIG. 1 is a graphical representation of the chromatogram of commercially available FSH-P on QAE-Sephadex A-50. The column dimensions were 5×33 cm. A sample load of 10 gm FSH-P was dissolved in 120 ml starting buffer (20 mM ammonium acetate, pH 7.2 and was applied to the column. The column was developed with 4.6 liters of starting buffer to elute the pLH in the sample (Peak A). Elution with 250 mM ammonium acetate was then begun and the pure FSH (FSH-W) fraction was collected (Peak C). The post-LH fraction is labeled peak B and the post-FSH is labeled peak fraction D.
Figure 2:
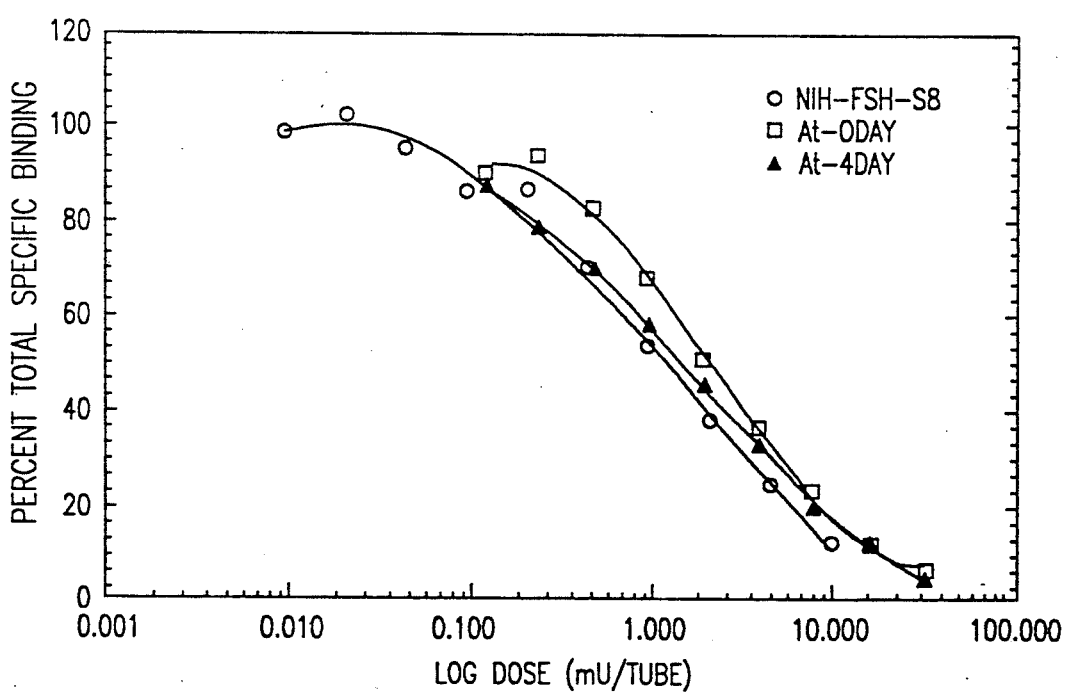
FIGS. 2 through 7 illustrate percent total specific binding plotted against log dose for each FSH batch in phosphate buffered saline (PBS) with and without thymol comparing zero days, four days, and the NIH-FSH-S8 standard. The curves are nearly identical in each case, indicating that there has been no change in FSH activity by placing in the PBS solution 1% by weight Thymol.
Figure 3:
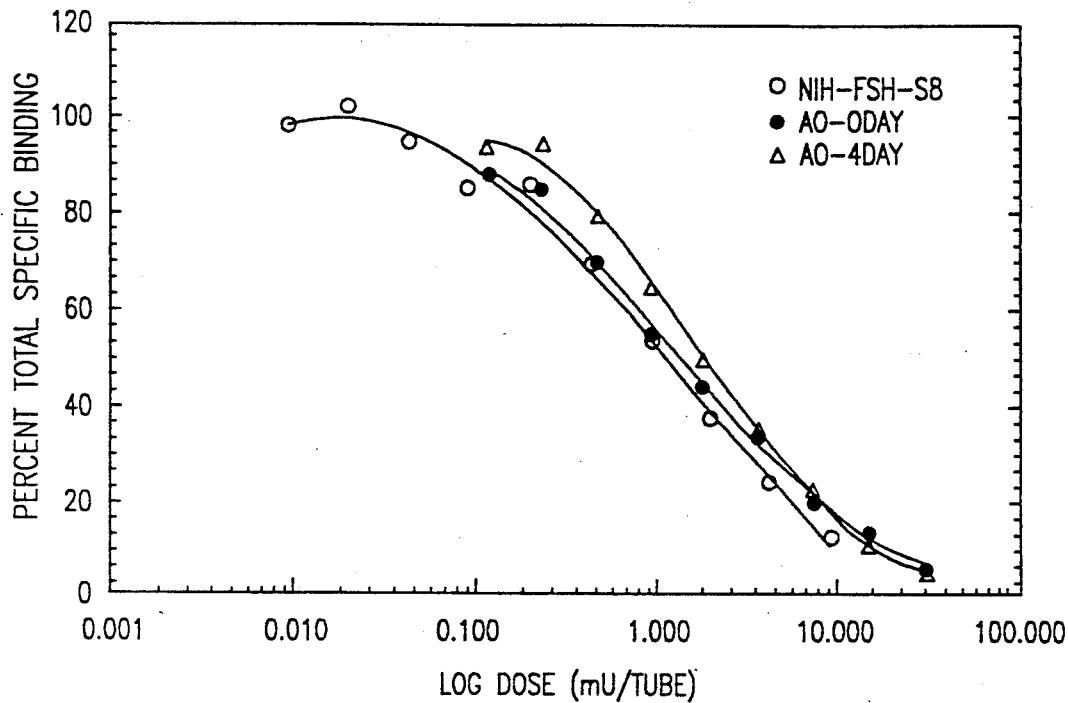
Figure 4:
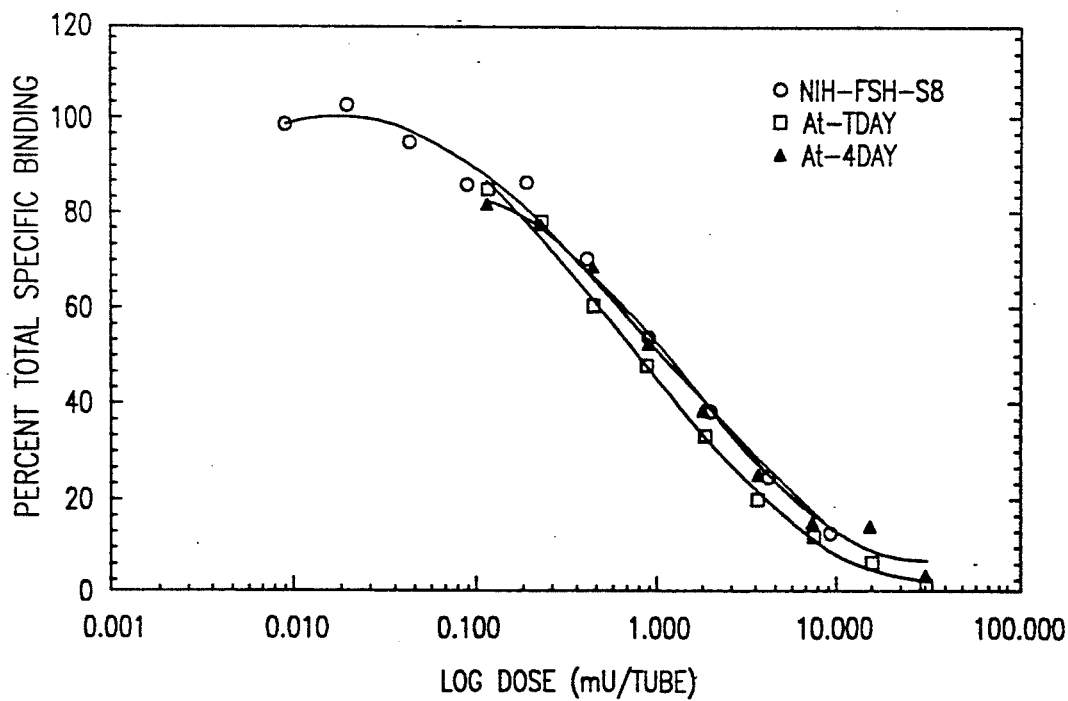
Figure 5:
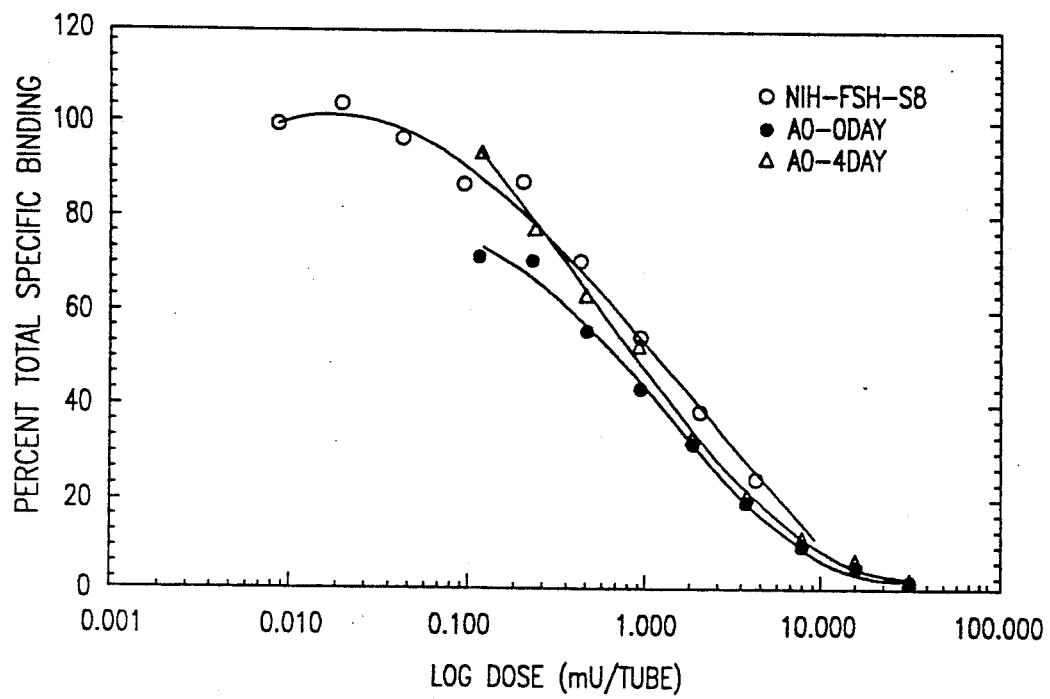
Figure 6:
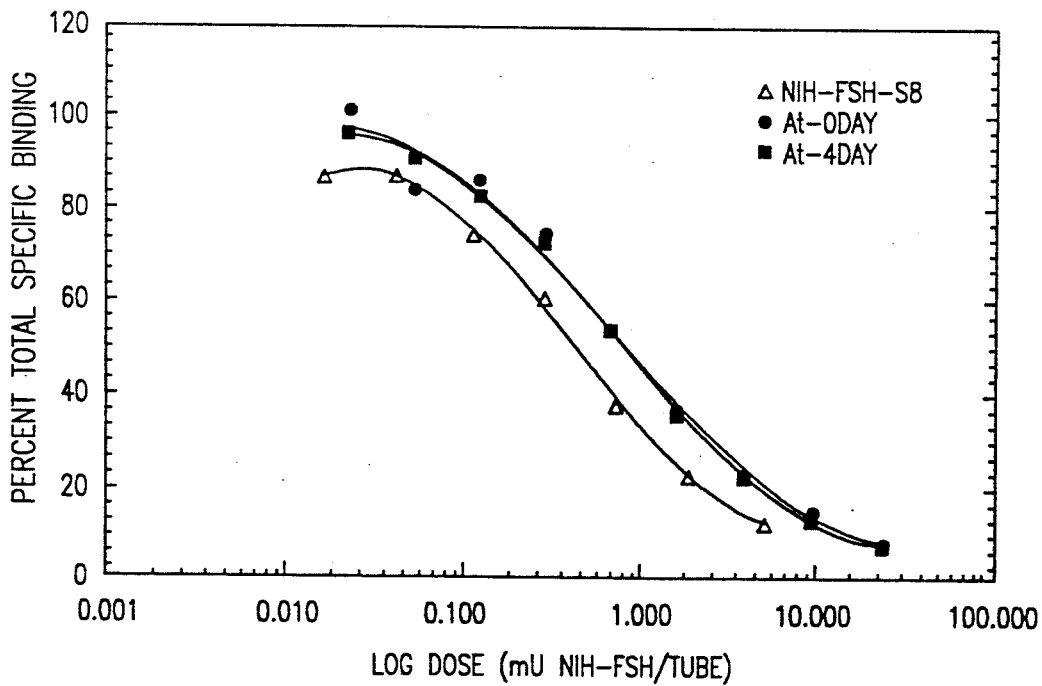
Figure 7:
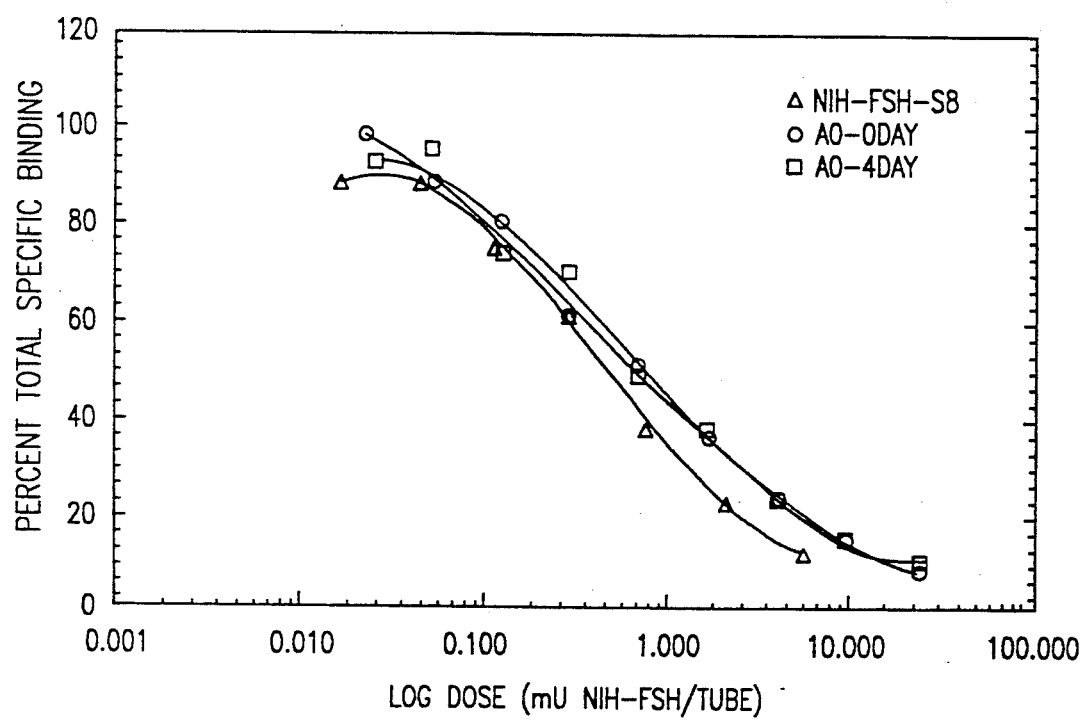

The present invention relates to a hormone composition and method for producing an optimum superovulation response in mammals.

The composition of the present invention resulted from the discoveries that high levels of progesterone at estrus reduce fertilization rates in cows and that treatment of cows with commercially available FSH preparations (FSH-P) elevates blood progesterone levels during estrus. Accordingly, while FSH-P may induce many follicles to ovulate during superovulation, fertilization of the ova is reduced by the elevation of blood progesterone levels during estrus.

It was thought that LH contamination of FSH-P was one of the likely causes of the abnormally high preovulatory progesterone levels in cattle. To test this theory, LH was removed from FSH-P and cattle were treated with the FSH-rich preparation. Better results were achieved with the FSH-rich preparation in terms of fertilization while the total ova produced decreased somewhat. It was then determined that by including a small amount of LH in the FSH preparation the recruitment of follicles was increased as expressed by total embryos recovered. Accordingly, it was deduced that the amount of LH in the FSH preparation had to be optimized in order to maximize both follicle recruitment and fertilization rates during superovulation in mammals.

The composition of the present invention, preferably, has a FSH/LH ratio of from about 500 to about 30,000 to maximize follicle recruitment and fertilization rates during superovulation in cattle. The composition of the present invention, most preferably, has a FSH/LH ratio of from about 1000 to about 23,000.

The composition of the present invention is, preferably, given to mammals by injection. A parenteral solution of the composition of the present invention is preferably prepared by forming a solution of the composition of the present invention with saline or phosphate buffered saline (PBS) with thymol. The composition of the present invention is given to cattle, for example, at a dose rate of 75 units (NIH-FSH-S1) by eight equal injections of 9.375 units over a period of 4 days at approximately 12 hour intervals.

The present invention will be described in more detail with reference to the following examples. These examples are merely illustrative of the present invention and are not intended to be limiting.

EXAMPLE 1

Use of Porcine Follicle Stimulating Hormone After Chromatographic Purification in Superovulation of Cattle An FSH-rich fraction hereinafter referred to as (FSH-W), free of detectable LH, was used to superovulate cattle. Three experiments were conducted to determine the optimal dose and treatment regimen for FSH-W, to compare FSH-W and FSH-P (a commercial preparation available from Burns Biotec, Omaha, Nebr.), and to study the effects of adding luteinizing hormone (LH) to the FSH-W.

Brahman crossbred cows were used in all experiments. The cattle were managed and superovulated in a similar manner as previously described in Donaldson, *Theriogenology* 21:517–524 (1984). The superovulation treatment was conducted over a period of 4 days and cows were treated twice daily at approximately 7 AM and 6 PM each day. Estrus was controlled with prostaglandin $F_{2a}$ (PGF, available from the Upjohn Co., Kalamazoo, Mich.) given in three doses of 35/15/15 mg morning, noon, and night on the third day, or with a cloprostenol dose (Estrumate, Haver Lockhart, Shawnee, Kans.) of 2.0 cc on the morning of the third day of superovulation as described in Donaldson, *Theriogenology* 21:1021–1022 (1984).

Estrus was monitored three times per day for about 45 minutes and the cows were bred about 6, 18 and 32 hours after detection of estrus. Embryos were collected nonsurgically and classified on the basis of microscopic appearance into transferable and nontransferable, unfertilized and fertilized degenerate (Donaldson, *Theriogenology* 21:517–524 (1984)). A transferable embryo appeared vital and was usually symmetrical and approximately round. The blastomeres were distinct with smooth membranes, without vesicles or excessive cellular debris beneath the zona pellucida. Non-transferable (degenerate) embryos had any or several of the following features: flattened, fuzzy membranes; grainy or dark appearance; cracked or broken zona. A fertilized degenerate embryo had clear evidence of cleavage whereas unfertilized eggs had perfectly spherical zonas containing single cells without evidence of cleavage. Embryo collection was performed on those cows that came into estrus. The data were analyzed by one- or two-way analysis of variance (ANOVA). Variance is represented by standard deviations of the mean.

The FSH-W preparation was produced from a commercially available porcine pituitary gland preparation (FSH-P, Lots 550C81 and 551C81 from Burns Biotec, Omaha, Nebr.) by employing a QAE-A50 chromatography step procedure that separates pLH from pFSH (S. D. Glenn, unpublished). The FSH-W preparation can also be produced by the same chromatography step procedure from the pituitary glands of domestic animals such as sheep and pigs. First, however, the FSH must be removed from the pituitary gland. This process involves taking a pituitary gland from an animal and either fresh freezing it or lyophilizing it. If the pituitary is fresh frozen the water is removed by acetone drying. Next, the acetone dried powder or freeze dried powder is extracted four times with a varying ratio of ethanol and tris buffer starting at 75% ethanol and working down to 20%. Each extract is then processed to remove the FSH and LH from the extract which is accomplished by cutting the extract with membranes by putting it through a 0.2 filter to remove all the fats, putting it through a 100,000 filter to remove all the proteins and other components greater than 100,000 Daltons and finally putting it over a 10,000 Dalton membrane to concentrate the volume. The concentrated solution is then freeze dried or placed directly on the QAE-A50 column. The procedure exploits the differential affinity of LH and FSH in a low ionic strength buffer such as 20 mM ammonium acetate at a pH of 7.2 to separate the LH and the FSH. The LH fraction contains some FSH activity, whereas the FSH fraction contains no detectable LH activity. The column elution is continued with 20 mM ammonium acetate at a pH of 7.2. After this step, the FSH activity retained on the column (approximately 66% of the total) is eluted with a 250 mM ammonium acetate buffer, pH 7.2. An inactive post-FSH fraction may be eluted with 500 mM ammonium acetate buffer, pH 7.2, if the remaining protein is to be accounted for.

With Lot 551C81, a 1.8-gm QAE-A50 column chromatography load was used. To obtain more material, the chromatography load was scaled up five-fold and a 10-gm load of Lot 565F82 was processed to obtain material of similar potency. The FSH and LH activity was assayed by a radioligand procedure as described previously by Bousfield et al., *J. Biol. Chem.*, 259:1911–1921 (1984). The receptor assays used $^{125}I$-labeled hCG or equine FSH as radioligands and rat testis (Moore et al., J. Biol. Chem. 255, 6930–6936 (1980)) or chicken testis homogenate (Glenn et al., Biol. Reprod. 24 (Suppl. 1) 117A Abstr. (1981)) as receptor preparations, respectively. The hormones were labeled to a specific activity of 25 to 50 Ci/ g. Under these conditions, the assay is linear for porcine FSH in the range of 2 to 200 ng of pure porcine FSH. The LH radioligand assay is linear over the range of 10 to 1000 ng of pure porcine LH. All potency estimates were made from the parallel portion of the competitive binding curves for the unknown. Relative potencies were calculated from the $ID_{50}$s determined from the inhibition curves (Liu et al., J. Biol. Chem. 249:5544–5550 (1974)). Potency was expressed in terms of the NIH-LH-S16 reference preparation for LH and NIAMDD-OFSH-13 reference preparation for FSH. Potency is expressed with these preparations equal to one unit by definition. The NIH-LH-S16 is essentially equipotent to the NIH-LH-S1 preparation. However, the NIAMDD-OFSH-13 is approximately 15 times the potency of the NIH-FSH-S1 preparation. The potency estimates for the hormones used in the experiments are shown in Table 1.

TABLE 1

| Separation and assay of FSH-W from FSH-P | | | |
|---|---|---|---|
| Lot No. of FSH-P | | 551C81 | 565F82 |
| FSH-P, starting wt., gm | | 1.8 | 10.0 |
| FSH-W | gm | 0.8313 | 3.485 |
| LH fraction | gm | 0.8097 | 0.8640 |
| Post-FSH fraction[a] | gm | | 2.089 |
| Recovery | % | 91.1 | 64.5 |
| Relative potencies[b] | | | |
| FSH-P | FSH | 0.32 | 0.35 |
| | LH | 0.039 | 0.075 |
| FSH-W | FSH | 0.5 | 0.66 |
| | LH | <0.005 | <0.011 |

[a]An inactive fraction eluted after the FSH, with 500 mM ammonium acetate.
[b]Relative to National Institutes of Health standards NIAMDD-OFSH-13 and NIH-LH-S16.

The elution pattern for the material coming off the QAE-A50 column is typical and is depicted in FIG. 1. The FSH-rich fraction (FSH-W) had a biological activity of $0.66 \times$ NIAMDD-OFSH-13 with an undetectable LH potency (i.e., it was less than $0.011 \times$ NIH-LH-S16, the limit of detection in the assay at the highest dose tested). The recovery of material from the columns was 91.1 and 64.5%.

Although the FSH-rich fractions are essentially free of LH, the FSH-W does not represent pure procine FSH. Pure porcine FSH has a potency of about seven times NIAMDD-OFSH-13 (Closset et al., Eur. J. Biochem. 86:105–113 (1978); Whitley et al., Endocrinology 102:1874–1886 (1978)). Thus, the fractions obtained here are about 11% pure but are suitable for the studies undertaken.

EXPERIMENT 1

120 cows were used in a $3 \times 2$ factorial design to test the effects of dose rate of FSH-W and treatment regimen on embryo production. The dose rates used were 2.7, 5.4, and 10.8 units (NIAMDD-OFSH-13). These dose rates were calculated from the potency estimates to be equipotent in FSH with 14, 28, and 56 mg (Armour units) FSH-P. The two treatment regimens consisted of eight individual injections of one-eighth of the total dose (constant regimen) or a descending dose of 19, 14, 10, and 7% of the total dose given twice a day for 4 days. Between 5 and 20 cows per week were assigned to experimental treatments. Treatments were assigned randomly to weeks and within weeks to each cow. Usually two treatments were assigned per week, but each treatment was represented within at least 2 wk.

The results of Experiment 1 are found in Table 2 below.

TABLE 2

Effects of FSH-W dose rate and treatment regimen on Mean Embryo Production (Experiment 1)

| | Embryo Production (Mean ± SD) | | | |
|---|---|---|---|---|
| Treatment | Number transferable | Total recovered | Percent transferable | Number fertilized |
| Dose × regimen | | | | |
| 2.7 units (NIH)[a] Constant | 4.7 ± 3.9 | 9.1 ± 7.2 | 66 ± 36 | 6.2 ± 5.0 |
| 2.7 units Descending | 4.2 ± 3.0 | 6.8 ± 4.5 | 67 ± 33 | 5.7 ± 3.6 |
| 5.4 units Constant | 7.8 ± 7.3 | 15.4 ± 18.0 | 64 ± 32 | 10.1 ± 10.6 |
| 5.4 units Descending | 6.4 ± 5.1 | 12.3 ± 8.1 | 51 ± 27 | 10.3 ± 6.7 |
| 10.8 units Constant | 4.3 ± 4.8 | 10.1 ± 8.6 | 35 ± 25 | 6.6 ± 6.9 |
| 10.8 units Descending | 1.8 ± 1.7 | 12.5 ± 8.8 | 19 ± 22 | 3.3 ± 3.1 |
| Both regimens (constant and descending) | | | | |
| 2.7 units | 4.5 ± 3.5 | 8.0 ± 6.2 | 66 ± 35 | 5.9 ± 4.4 |
| 5.4 units | 7.0 ± 6.5 | 13.8 ± 14.6 | 57 ± 31 | 10.1 ± 9.1 |
| 10.8 units | 3.1 ± 3.9 | 11.2 ± 8.8 | 27 ± 25 | 5.1 ± 5.8 |
| All doses (2.7, 5.4, and 10.8 NIH units) | | | | |
| Constant | 5.6 ± 5.8 | 11.5 ± 12.6 | 56 ± 35 | 7.6 ± 8.1 |
| Descending | 4.3 ± 4.0 | 10.7 ± 7.9 | 46 ± 34 | 6.7 ± 5.5 |
| BY ANOVA P = | 0.003 | 0.053 | 0.001 | 0.004 |
| Dose | | | | |
| Regimen | 0.126 | 0.678 | 0.089 | 0.652 |
| Interaction | 0.696 | 0.527 | 0.580 | 0.527 |

[a]National Institutes of Health.

There was a significant effect of dose of FSH-W on the number of transferable embryos recovered (P=0.003). The number of transferable embryos increased from 4.5±3.5 to 7.0±6.5 and then decreased to 3.1±3.9 with increasing dose. The total embryos recovered increased from 8.0±6.2 to 13.8±14.6 and then to 11.2±8.8 (P<0.001) with increasing dose, while the percent transferable declined from 66±35% to 57±31% and then to 27±25% (P=0.001). These changes in the number and percent transferable were associated with changes in the number of fertilized embryos; this number increased from 5.9±4.4 to 10.1±9.1 and then declined to 5.1±5.8 (P=0.004). The number of fertilized embryos that degenerated was not affected by the dose of FSH-W (1.4±2.5, 3.1±3.7, and 2.0±3.0, respectively; P=0.120). There were no significant interactions between dose and regimen.

EXPERIMENT 2

130 cows were used to compare FSH-W made from Lot 551C81 with FSH-P (Lot 551C81). The dose of FSH-W that gave the best embryo production response in the first experiment (5.4 mg) was compared with the dose of FSH-P (28 mg, Armour units) that was previously reported to give the best response (Donaldson, Theriogenology 22:-205-212 (1984)). The cows were treated with a descending dose treatment regimen in which 19, 14, 10, and 7% of the total dose was given twice a day for 4 days. Cows were assigned randomly to the two treatments. Jugular blood samples were taken at the beginning of estrus for progesterone determinations in accordance with the procedure described by Reimers et al., J. Anim. Sci. 57:683–691 (1983), from 15 cows superovulated with FSH-P (28 mg) and from 24 cows superovulated with FSH-W (5.4 mg).

The results of Experiment 2 are found in Table 3 below:

TABLE 3

Comparison of FSH-W and FSH-P for the Superovulation of Cattle

| Embryo Parameters | FSH-P Mean | FSH-P SD | FSH-W Mean | FSH-W SD | P |
|---|---|---|---|---|---|
| Number transferable | 2.9 | ± 4.0 | 6.3 | ± 6.7 | 0.001 |
| Total recovered | 11.1 | ± 10.0 | 12.1 | ± 9.6 | 0.591 |
| Percent transferable | 30 | ± 33 | 47 | ± 35 | 0.007 |
| Number fertilized | 5.8 | ± 6.7 | 9.0 | ± 8.2 | 0.019 |
| Number degenerate | 2.4 | ± 3.6 | 2.5 | ± 3.0 | 0.819 |

When compared with 28 mg FSH-P, 5.4 units FSH-W significantly increased the number of transferable embryos from 2.9 to 6.3 (P=0.001) without affecting the total embryos recovered (12.1 and 11.1, P=0.591).

5.4 units of FSH-W was calculated to be equipotent with 28-mg equivalents of Armour units of FSH-P, and as noted above these dose levels have been found to be the most effective doses for both products. The percent transferable was higher in the FSH-W (47%) than in the FSH-P treated cows (30%, P=0.007). This higher percentage resulted from an increase in the number of embryos fertilized from 5.8 to 9.0 (P=0.019).

The blood progesterone levels (ng/ml) during estrus in the 15 cows treated with FSH-P (0.88±0.69) were significantly higher (P=0.016) than in the 24 cows treated with FSH-W (0.45±0.36). Normal blood progesterone levels in the cow during estrus range from 0.2 to 0.5 ng/ml (Lemon et al., J. Reprod. Fertil. 31:501-502 (1972)).

Crisman et al. (Theriogenology 15:141-154 (1980)) showed that excess progesterone (but not estradiol) increased ovum transport rates in the cow. The higher progesterone levels in the FSH-P treated cows may be caused by the LH contamination, which enhances progesterone production in the theca interna of preantral follicles (Terranova et al., Biol. Reprod. 29:630-636 (1983)) or which luteinizes large follicles that subsequently produce progesterone. FSH can stimulate progesterone production in follicles itself (Lischinsky et al., Endocrinology 113:1999-2003 (1983)) and this progesterone production may be involved in the reduction in the number of fertilized embryos with higher doses of FSH-W. Previously, high blood progesterone levels at estrus have been associated with decreased embryo production Zin cattle (Greve et al., Theriogenology 21:238 Abstr. (1984).

EXPERIMENT 3

50 cows were used in a 2×2 factorial design to test the effects on embryo production of adding LH (made from Lot 551C81 as described above) to the FSH-W preparation on the first day of FSH treatment to induce superovulation. The two dose levels of FSH-W were 5.4 and 8.3 units given in a constant regimen as in Experiment 1. LH was injected at the time of the two FSH-W injections at dose rates of 0 or one mg NIH-LH-S16. This LH included 0.06 units of FSH per injection as a contaminant. Cows were assigned randomly to the four treatments.

The results of Experiment 3 are found in Table 4 below:

TABLE 4

Effect of adding LH to FSH-W on Mean Embryo Production

| Treatment | Number transferable | Total recovered | Percent transferable | Number fertilized |
|---|---|---|---|---|
| Dose × LH | | | | |
| 5.4 units (NIH)[a] + LH | 5.1 ± 3.2 | 10.8 ± 4.6 | 55 ± 34 | 7.6 ± 3.4 |
| 5.4 units NO LH | 7.8 ± 4.4 | 13.4 ± 5.5 | 60 ± 28 | 11.1 ± 5.3 |
| 8.3 units + LH | 3.6 ± 6.3 | 10.8 ± 7.8 | 41 ± 37 | 2.7 ± 1.7 |
| 8.3 units NO LH | 7.8 ± 7.7 | 16.7 ± 9.9 | 45 ± 28 | 14.7 ± 10.1 |
| Both LH treatments | | | | |
| 5.4 units | 6.4 ± 4.1 | 12.1 ± 5.2 | 55 ± 31 | 9.3 ± 4.8 |
| 8.3 units | 5.8 ± 7.4 | 13.9 ± 9.4 | 43 ± 33 | 8.7 ± 9.4 |
| Both doses | | | | |
| LH | 4.4 ± 5.0 | 10.8 ± 6.3 | 48 ± 36 | 5.3 ± 3.6 |
| NO LH | 7.8 ± 6.3 | 15.0 ± 8.1 | 53 ± 29 | 12.8 ± 8.1 |
| ANOVA P = LH | 0.052 | 0.06 | 0.635 | 0.001 |
| Dose | 0.698 | 0.525 | 0.126 | 0.742 |
| Interaction | 0.665 | 0.529 | 0.945 | 0.024 |

[a] National Institutes of Health.

Adding LH to the FSH-W on the first day of FSH treatment reversed the effect of removing LH from FSH-P. The number of transferable embryos were reduced from 7.8±6.3 to 4.4±5.0 (P =0.05, Table 4). Total embryos recovered was reduced (P=0.06), and percent transferable was not significantly different (P=0.635). The number of fertilized embryos was reduced from 12.8±8.1 to 5.3±3.6 by the addition of LH dose to FSH-W (P<0.001). There was a significant interaction (P=0.024); LH had more effect on fertilization at the higher dose. Added LH significantly reduced the number of fertilized degenerating embryos (4.8±3.9 to 1.5±1.6, P=0.001), but the percent degenerate (31±31 and 38±28%, P=0.55) remained the same because there was a parallel reduction in the number of fertilized embryos.

The effect of altering the LH content of the FSH on total embryo production was not clear, but embryo recovery is not a sensitive measure of ovulation rate because only about 40% of the ovulations are represented by embryos recovered (Donaldson, Vet. Rec. 117:33-34, 1985).

In cattle superovulated with FSH-P, fertilization rates have been found not to be improved by increasing the number of times a superovulated cow was bred above two times or by increasing the number of straws of semen used at each breeding above one (Critser et al., Theriogenology 13:397-405 (1980); Donaldson, Vet. Rec. 117:35-37 (1985). Based on these results, it was hypothesized that there are factors other than sperm numbers that interfere with fertilization. In the normal estrus cycle, the LH surge triggers the maturation phase of the oocyte, establishing the time frame for fertilization (Moor et al., Theriogenology 21:103-1-16 (1984)). Excess LH in a superovulatory hormone causes premature stimulation of the oocyte (Moor et al., Theriogenology 21:103-116 (1984)) so that the oocyte may not be capable of being fertilized at the normal time. In ewes, superovulation reduces sperm transport (Armstrong et al., Proc. 10th Inter. Cong. Anim. Reprod. Art. Insem., Urbana, IL, 1984, pp. VII-8-VII-15). In rats, oocytes produced after superovulation with pregnant mare serum gonadotropin are normal (Evans et al., J. Reprod. Fertil. 70:131-135 (1984)) but have reduced fertility due to complete or partial failure of fertilization (Walton et al., J. Reprod. Fertil. 67:91-96 (1983); J. Reprod. Fertil. 67:309-314 (1983)). Therefore, the demonstrated increase in blood progesterone levels at estrus offers several mechanisms whereby fertilization rates could be influenced by the levels of LH and FSH in the superovulation treatments namely, increased tubal transport of ova, decreased sperm capacitation, or decreased sperm transport. LH in superovulation regimens appears to be deleterious and exerts its effect at several stages in the reproductive process. Excluding LH from an FSH preparation for superovulating cattle increased the production of transferable embryos by increasing the number of fertilized embryos.

EXAMPLE 2

Dose Response to FSH-W With and Without LH Contamination

FSH-P (lot 565F82, Burns Biotec, Omaha Nebr.) was separated into an FSH-W fraction without any detectable LH using sephadex QAE-A50 column chromatography as described in Example 1. The relative potency of FSH and LH for the FSH-P (0.32 and 0.039) and FSH-W (0.66 and <0.01) fractions to NIH-FSH-S13 and NIH-LH-S16 were determined using chicken and rat testicular homogenate receptor assays. The assays indicated that 5.4 units FSH-W was approximately equipotent in FSH to 20 Armour units (often expressed as mg) FSH-P. The dose response to FSH-P was measured in 80 Brahman cross cows (20 per dose level) and to FSH-W in 140 Brahman cross cows (37, 36, 27, 31 and 9 per dose within increasing doses respectively).

The results of this study appear in Table 5 below.

TABLE 5

| FSH-W MEAN EMBRYOS/COW | | | | FSH-P MEAN EMBRYOS/COW | | | |
|---|---|---|---|---|---|---|---|
| FSH units | #trans-ferable | total | % trans-ferable | Ar-mour units | #trans-ferable | total | % trans-ferable |
| 2.7 | 4.5 | 8 | 66 | | | | |
| 5.4 | 7.1 | 14. | 57 | 20 | 2.1 | 2.6 | 72 |
| 8.3 | 4.9 | 11 | 46 | 28 | 3.9 | 10.1 | 47 |
| 10.8 | 3.4 | 11.2 | 29 | 40 | 2.5 | 8.2 | 35 |
| 16.2 | 3.5 | 9.4 | 35 | 60 | 0.9 | 6.3 | 16 |
| By ANOVA within columns | | | | | | | |
| P = | 0.043 | 0.161 | 0.000 | | 0.006 | 0.003 | 0.000 |

The removal of the LH increased the effectiveness of the FSH-W by lowering the dose giving the maximum response, and by apparently increasing the number of transferable embryos produced at that response. The decline in embryo production beyond the most effective dose was not as large with FSH-W as it was with FSH-P. Removal of the LH from the FSH-P altered the shape of the dose response curve, and increased the responsiveness of the cow to FSH.

EXAMPLE 3

Effects of LH on Embryo Production in Superovulated Cows

As noted above, it has been shown that normal preovulatory progesterone (P4), LH and FSH concentrations are necessary for optimal embryo production from superovulated cows. Abnormal concentrations of P4, LH and FSH are followed by abnormal follicular-/oocyte maturation and lowered embryo production. Since LH contamination of FSH preparations is thought to be one of the likely causes of abnormal preovulatory progesterone concentrations, this example was designed to study the effects of LH added to FSH on embryo production in the cow.

In this study, three FSH preparations were used, FSH-P (available from Burns Biotec Omaha Nebr.), FSH-W and FSH-S. FSH-W was produced as described in Example 1 from FSH-P or from porcine pituitaries and contained no detectable LH. The FSH and LH activity of the FSH-W and three of six lots of FSH-P used in this study were assayed by a radioligand receptor assay using $^{125}$I-labelled HCG or equine FSH as radioligands (Bousfield et al., J. Biol. Chem. 259, 1911 (1984)) and rat testis (Moore et al., J. Biol. Chem. 255, 6930 (1980)) or chicken testis (Glenn et al., Biol. Reprod. 24 (Suppl. 1) 117A (1981)) homogenates as receptor preparations respectively. Potency was expressed in terms of NIH-LH-S1 and NIH-FSH-S1 preparations. FSH/LH ratios were calculated in terms of these units. FSH-S was made from FSH-W by adding an aliquot of FSH-P to achieve an FSH content per dose of 75 units with an FSH/LH of greater than 500 and less than 2000.

A total of 273 cows were superovulated at seven embryo transfer centers. At each of the centers FSH-W was substituted for the FSH-P that was in normal use. At two centers FSH-S was also substituted. These superovulations using FSH-W and FSH-S were compared with contemporary controls receiving FSH-P. Cows from a wide range of cattle breeds (both beef and dairy) were superovulated with 75 or 112 units FSH-W, FSH-S or FSH-P (28-42 mg Armour units). Five centers used 75 units and two centers used 112 units. The total number of embryos and ova, the number of transferable embryos, the number fertilized and the number of fertilized degenerates were recorded (Donaldson Vet. Rec. 117, 35 (1985). Superovulation techniques varied from center to center but generally followed the non-surgical technique described by Elsden et al., Theriogenology 6, 523 (1976).

The data were collected over an 18 month period and no efforts were made to detect or correct for variations in techniques between centers. It was assumed that the FSH-P preparations used and not assayed had similar FSH/LH ratios to the lots that were assayed. The ratios of percent transferable, percent fertilized and percent fertilized degenerate were calculated for each observation. The data were analyzed by analysis of variance and Student's two tailed t test between centers and then pooled over all centers and both FSH doses.

The results of this study appear in Table 6 below.

TABLE 6

| EFFECT OF LH ON EMBRYO PRODUCTION IN SUPEROVULATED COWS (MEANS ± S.D.) | | | | |
|---|---|---|---|---|
| | FSH-W | FSH-S | FSH-P | P< |
| FSH/LH | >20,000 | >500 | <100 | |
| # COWS | 94 | 89 | 90 | |
| EMBRYOS | | | | |
| TOTAL | 8.8 + 7.4 | 10.6 + 9.2 | 8.1 + 7.2 | 0.108 |
| FERTILIZED | 7.6 + 7.3 | 9.0 + 8.5 | 6.0 + 6.6 | 0.040 |
| TRANSFERABLE | 5.7 + 5.8 | 5.8 + 6.4 | 3.3 + 4.7 | 0.006 |
| % TRANSFER-ABLE | 66 + 33 | 51 + 35 | 37 + 38 | 0.001 |
| % FERTILIZED | 83 + 28 | 81 + 29 | 62 + 42 | 0.001 |
| % FERTILIZED | 21 + 27 | 34 + 30 | 39 + 37 | 0.002 |

TABLE 6-continued

EFFECT OF LH ON EMBRYO PRODUCTION
IN SUPEROVULATED COWS (MEANS ± S.D.)

| | FSH-W | FSH-S | FSH-P | P< |
|---|---|---|---|---|
| DEGENERATE | | | | |

There was no statistical difference in embryo production between centers within FSH preparations and between dose rates, so the data was pooled. FSH-S produced an average of 10.6 embryos and ova per flush which was not significantly different from the 8.8 and 8.1 produced by FSH-W and FSH-P ($P<0.108$). The addition of LH below the FSH/LH of 500 significantly reduced the number of embryos of transferable quality from 5.7 (FSH-W), and 5.8 (FSH-S) to 3.3 (FSH-P, $P<0.006$). As LH levels increased the transferable percent declined from 66% (FSH-W), to 51% (FSH-S) and 37% (FSH-P, $P<0.001$) because of changes in the number of embryos fertilized and an increase in the percent of fertilized embryos that degenerated. The number of fertilized embryos increased from 7.6 (FSH-W) to 9.0 (FSH-S, $P>0.01$) and then declined significantly to 6.0 with FSH-P ($P<0.04$). The percentage of fertilized embryos that degenerated increased from 21% (FSH-W) to 34% (FSH-S, $P<0.032$) and then to 39% (FSH-P, $P<0.002$) as LH levels in the FSH preparations increased.

The precision of this study may have been reduced because of the involvement of seven different embryo transfer centers, but the results suggest important differences exist between the superovulation response produced by these three hormone preparations, which differed only in their LH content.

The dose rates for each FSH preparation were selected to be equipotent in FSH and to be optimum for transferable embryo production (Donaldson, Theriogenology 22:205 (1984); Donaldson et al., Theriogenology 23, 189 (1985)). LH contamination of FSH reduced the fertilization rates of ova produced by superovulation. LH appears to specifically block fertilization, the mechanism for which may be through premature stimulation of the maturing oocyte (Moor et al., Theriogenology 21, 103 (1984)) so that the oocyte is not capable of being fertilized. This is supported by an earlier study that showed that fertilization problems in superovulated cows cannot be overcome by multiple inseminations with many doses of semen (Donaldson, Vet. Rec. 117, 35 (1985)). The number of times that the cows were bred and the quantity of semen used was not standardized in this experiment, but the routine practice at all but one of the embryo transfer centers was to breed superovulated cows at least twice with a total of at least two doses of semen. The slight increase in the number of fertilized embryos in the FSH-S group was offset by the increase in the degeneration of fertilized embryos with increasing LH levels. The mechanism by which fertilized embryos degenerate with increasing LH levels is not known. As the LH content of the FSH increased, the variability of some of the responses increased as measured by the standard deviation of the mean. This was seen in the number and percentage transferable, and the number and percentage fertilized. Thus, the variability of superovulation response may be reduced by controlling the LH levels in the superovulatory hormones.

There are problems comparing the assay results from different laboratories of various gonadotropin preparations used in the superovulation of cattle because of the variety of assays and standards used. It appears that all FSH-P preparations have an FSH/LH of less than 100. These results confirm the conclusions drawn from endocrine data (Donaldson, Theriogenology 23, 441 (1985) and Calleson et al., Theriogenology 25, 71 (1986)) that the traditional superovulatory treatments with gonadotropins containing LH disturbs the normal oocyte and follicular development leading to oocytes of inferior quality; and that FSH is mainly responsible for the number of embryos and ova produced and LH for their subsequent quality.

EXAMPLE 4

LH Effects on Superovulation and Fertilization Rates

The effects of LH during superovulation and at the subsequent estrus were studied in 108 beef and dairy cows. The experimental design was a 3×2 factorial with three FSH preparations, having different concentrations of LH, and two levels of LH (10 and 0 units) injected six hours after the onset of estrus. The FSH preparations were FSH-W, FSH-S and FSH-P. The FSH-W and FSH-S were prepared from FSH-P (Armour Pharmaceutical Co., Chicago, Ill.) as described in Examples 1 and 3, respectively.

The hormones were assayed by radioligand receptor assay referenced to the NIH-FSH-S1 and NIH-LH-S1 standards. The FSH/LH ratios of the three FSH preparations were in the following ranges 30,000 (FSH-W), 1600 (FSH-S) and 114 (FSH-P).

The cows were superovulated with 75 units of FSH divided into eight equal doses administered at 12 hour intervals for four days starting in the evening. Chlorprostenol 2cc (Estrumate, Haver-Lockart, Shawnee, Kans.) was given at the time of the fifth FSH injection. The cows were observed closely for the onset of estrus, and half of them received 10 units LH six hours later. Cows were bred with one straw of frozen semen four to 22 hours after the onset of estrus. Embryos were recovered nonsurgically seven days later and the total, number transferable and the number fertilized recorded. Data were analyzed by two way analysis of variance.

Transferable/total embryos recovered were 2.4/4 (FSH-W), 6/10.5 (FSH-S) and 1.9/5.4 (FSH-P). Total and transferable embryos were significantly different ($P=0.011$ and $0.014$). The percent transferable was lower in the FSH-P (35%) than in the other groups (55% and 52%, $P=0.047$). The LH effect was in the percent fertilized, being 84% (FSH-S), 80% (FSH-W) and 48% in the FSH-P group ($P=0.001$). LH at estrus did not affect transferable or total embryos (3.5/7 with LH and 4.9/8.5 in controls, $P=0.667$ and $0.756$). The percent of ova fertilized in the LH at estrus group (70%) tended to be lower than the controls (82%, $P=0.08$), as did the percent transferable (43% versus 56%, $P=0.153$). Embryo production was significantly affected by the LH levels in the FSH but not by the LH injected at estrus. High levels of LH in the FSH reduced fertilization rates. Low fertilization rates have traditionally been approached by increasing the number of doses of semen used and the number of times a donor cow is bred. In this study one breeding with one dose of semen produced normal fertilization rates when the level of LH in the FSH hormone was reduced, indicating that low fertilization rates with FSH-P are specifically an LH problem not a semen quantity or a number of times bred problem.

EXAMPLE 5

Field Tests With Three FSH Preparations

The three FSH preparations were used almost exclusively on problem donors that had failed to respond to commercially available Armour FSH-P. Each embryo transfer center testing the preparations were asked to report contemporary results with FSH-P. The data are therefore heterogeneous and may be best used to demonstrate the type of results in independent hands and fertilization rates. The actual numbers and differences between treatments have to be interpreted with caution.

Three hormone preparations were tested each with a different formulation. They were:

FSH-W batches 200 and 167 of an FSH preparation containing no detectable LH or having a ratio of FSH/LH of 30,000.

FSH-S, an FSH preparation according to the present invention containing some LH having an FSH/LH ratio of 1610.

FSH-P is a commercial FSH preparation containing much LH having an FSH/LH ratio of <114.

The FSH-W and FSH-S preparations utilized in this study were prepared from FSH-P (Armour Pharmaceutical Co., Chicago, Ill.) as described in Examples 1 and 3, respectively.

The data represents most breeds. Six of the 10 embryo transfer centers only used FSH-W on problem cows and the production from these cows was less than with FSH-P. The others used FSH-W on the normal run of cows and they had production equal to or better than FSH-P. There were obvious differences between centers on classification of embryos into unfertilized and fertilized degenerate. No attempt has been made to correct data for any of these differences. Each center used at least 2 FSH products.

The data has been divided on the basis of product and dose. FSH-W and FSH-S have been measured in terms of the NIH-FSH-FSH1 standard. The three doses are 75, 112 and 150 units. (75 units is the same as 5 units S13, the units in which batch 200 was measured). The equivalent Armour units are 28, 42 and 56. Collections where no embryos were recovered are not included in this analysis, mainly because there seemed to be large irregularities in the way they were reported. It is not believed that the majority of zero collections have anything to do with the FSH, and their absence does not affect the fertilization and degeneration rates that were the focus of this example.

The data confirms the controlled experiments that FSH-W and FSH-S improved fertilization rates. This effect carries over into percent transferable, and in the case of FSH-S into the number transferable. FSH-S increased recruitment of follicles over FSH-W as expressed by the total embryos recovered. There is an indication that increasing the dose of FSH reduces the degeneration rate.

TABLE 7

EMBRYOS TRANSFERABLE/TOTAL (% TRANSFERABLE)

| PREPARATION | 75 | 112 | 150 | TOTAL |
|---|---|---|---|---|
| FSH-W | 4.8/9.4 | 4.7/7.2 | 5.4/8 | 4.9/8.9 |
|  | (55) | (70) | (62) | (58) |
| # FLUSHES | 158 | 26 | 46 | 229 |
| FSH-S | 7.5/11.4 | 7/15.1 | 8/11.5 | 7.5/12.2 |
|  | (64) | (46) | (71) | (62) |
| # FLUSHES | 34 | 11 | 12 | 57 |
| FSH-P | 5.2/11.4 | 4/8.8 | 6.3/10.1 | 5.4/10.8 |
|  | (48) | (55) | (54) | (50) |
| # FLUSHES | 157 | 26 | 60 | 243 |
| TOTAL | 5.2/10.5 | 5.0/9.5 | 4.5/9.4 | 5.3/10.1 |
|  | (53) | (59) | (60) | (55) |
| # FLUSHES | 349 | 63 | 117 | 529 |
| P VALUES DOSE | 0.566, | 0.081, | 0.549 | |
| PREPARATION | 0.029, | 0.087, | 0.138 | |

TABLE 8

EMBRYOS # FERTILIZED, % FERTILIZED

| PREPARATION | 75 | 112 | 150 | TOTAL |
|---|---|---|---|---|
| FSH-W | 6.4,73 | 5.8,80 | 6.8,82 | 6.4,75 |
| FSH-S | 10.4,95 | 9.9,91 | 11,88 | 10.5,92 |
| FSH-P | 7.2,65 | 5,65 | 7.2,63 | 7,64 |
| TOTAL | 7.2,71 | 7.4,73 | 6.2,76 | 7.1,72 |
| P VALUES DOSE |  |  | 0.586, | 0.966 |
| PREPARATION |  |  | 0.000, | 0.000 |

TABLE 9

EMBRYOS # FERTILIZED DEGENERATE, % FERT. DEGENERATE

| PREPARATION | 75 | 112 | 150 | TOTAL |
|---|---|---|---|---|
| FSH-W | 1.9,26 | 1.3,20 | 1.2,21 | 1.7,24 |
| FSH-S | 3.2,31 | 5.2,42 | 2.6,20 | 3.5,31 |
| FSH-P | 2.6,30 | 1,16 | 1,13 | 2,24 |
| TOTAL | 2.4,28 | 1.9,22 | 1.3,17 | 2.1,25 |
| P VALUES DOSE |  |  | 0.586, | 0.966 |
| PREPARATION |  |  | 0.000, | 0.000 |

EXAMPLE 6

This example compares a batch of FSH-S having a FSH/LH ratio of approximately 1000 and a batch of FSH-P having a FSH/LH ratio of approximately 114. The batch of FSH-S was prepared in accordance with the procedure described in Example 3.

The results of this comparison are shown in Table 10 below.

TABLE 10

| | N | # Good Embryos Mean ± SD | Total Embryos Mean ± SD | % Good Embryos Mean ± SD |
|---|---|---|---|---|
| FSH-S | 6 | 7.56 ± 6.98 | 14.2 ± 10.12 | 53.28 ± 31.64 |
| FSH-P | 6 | 4.39 ± 5.02 | 10.66 ± 7.82 | 42.56 ± 35.07 |

This example demonstrates that a reduction in LH content of the FSH preparation is beneficial in terms of the number of good embryos, the total embryos and percent good embryos.

An additional 239 cows were superovulated with (FSH/LH=22,900, 0.89% LH) based on a molecular basis, resulting in a recovery average of 6.1/11.2 embryos.

EXAMPLE 7

Duration-Efficacy Study

Objective. The objective of this study was to determine the optimum duration of treatment with FSH-S.

Cows were selected to go on experiment after they had been detected in heat with a normal estrus interval (16 to 24 days). Cows were put into experimental groups randomly on the basis of their estrus dates. On a weekly basis all the ear tag numbers of the experimental cows that had been in estrus during the preceeding week were written on a separate card and the cards were selected at random and allocated to successive groups within breeds. The cows were then scheduled for starting on treatment on a day convenient for the subsequent collection date.

Cows were treated for 3, 4 or 5 days with 18.75 units of FSH-S per day in equal divided doses morning and evening. This is the same rate as a total dose of 75 units over 4 days. The FSH-S used in this study was prepared in accordance with the procedure described in Example 3. Three separate batches of FSH-S were used to treat the cows for this study. These batches had FSH/LH ratios of 1500, 1443 and 1267, respectively.

Embryo production was measured in terms of total embryos and ova, and the number of transferable embryos.

The results of this study are shown in Tables 11 and 12 below.

TABLE 11

| Days of treatment with FSH | N | Transferable Embryos Mean ± SD | Total Ova + Embryos Mean ± SD |
|---|---|---|---|
| 3 | 20 | 1.250 ± 1.699 | 3.950 ± 4.295 |
| 4 | 20 | 5.950 ± 4.421 | 1.050 ± 7.074 |
| 5 | 20 | 5.550 ± 5.903 | 8.200 ± 5.836 |

TABLE 12

| Breed | N | Transferable Embryos Mean ± SD | Total Ova + Embryos Mean ± SD |
|---|---|---|---|
| Holstein | 28 | 5.036  4.851 | 7.536  4.917 |
| Beef | 32 | 3.563  4.763 | 7.906  7.670 |

There was no breed effect observed for either parameter measured. Treatment for 4 and 5 days produced more transferable and total embryos than did treatment for 3 days. Treatment for 4 days appeared to give the best overall results.

EXAMPLE 8

This example demonstrates a comparison of equipotent batches of FSH-W having a FSH/LH ratio of 30,000 and commercially available FSH-P having a FSH/LH ratio of 114. The FSH-W preparation was produced in accordance with the procedure described in Example 3. 130 cows were used to compare FSH-W and FSH-P given in equivalent doses, (5.4 units FSH-W and 28 mg. FSH-P) as eight descending injections (19, 14, 10 and 7%) twice a day for four days.

The results are shown in Table 13 below.

TABLE 13

| Embryos | FSH-P | FSH-W | P |
|---|---|---|---|
| N | 65 | 65 | |
| # transferable | 2.92 | 6.32 | 0.001 |
| total | 11.12 | 12.05 | 0.591 |
| % transferable | 30.02 | 46.87 | 0.007 |

TABLE 13-continued

| Embryos | FSH-P | FSH-W | P |
|---|---|---|---|
| # fertilized | 5.78 | 9.02 | 0.019 |
| % fertilized | 54.69 | 63.2 | 0.237 |
| # degenerate | 2.39 | 2.52 | 0.819 |
| % degenerate | 23.12 | 17.7 | 0.258 |

Cows superovulated with FSH-W performed significantly better in terms of # transferable embryos, % transferable embryos and # fertilized embryos. These results corroborate the results of Example 1.

EXAMPLE 9

Dose Response Study

The objective of this study was to establish the optimum dose for a FSH-S preparation having a FSH/LH ratio of 1610. The FSH-S preparation utilized in this study was prepared in accordance with the procedure described in Example 3.

Cows were selected to go on experiment after they had been detected in heat with a normal estrus interval (16 to 24 days). Cows were put into experimental groups randomly on the basis of their estrus dates. On a weekly basis all the ear tag numbers of the experimental cows that had been in estrus during the preceeding week were written on a separate card and the cards were selected at random and allocated to successive groups within breeds. The cows were then scheduled for starting on treatment on a day convenient for the subsequent collection date.

Sixty cows (24 Holstein and 36 beef) were superovulated with 37.5, 75 or 150 units of FSH-S (20 per treatment). The results of this study appear in Table 14 below. In another experiment 45 cows (all beef) were superovulated with 75, 112 or 150 units of FSH-S. The results of this study appear in Table 15 below.

The total embryos and ova and the number of transferable embryos were recorded.

TABLE 14

| Dose Rate | N | Transferable Embryos Mean ± SD | Total Ova + Embryos Mean ± SD |
|---|---|---|---|
| 37.5 | 20 | 1.850 ± 2.128 | 3.700 ± 3.770 |
| 75 | 20 | 6.000 ± 5.060 | 10.200 ± 5.913 |
| 150 | 20 | 5.300 ± 3.621 | 9.250 ± 3.300 |

TABLE 15

| Dose Rate | N | Transferable Embryos Mean ± SD | Total Ova + Embryos Mean ± SD |
|---|---|---|---|
| 75 | 15 | 6.067 ± 5.431 | 7.667 ± 5.802 |
| 112 | 15 | 5.667 ± 3.200 | 9.800 ± 6.190 |
| 150 | 15 | 5.067 ± 4.061 | 8.467 ± 7.396 |

As shown in Table 14, the 75 and 150 units FSH-S produced significantly more transferable and total embryos than did 37.5 units. Also, as shown in Table 14, there was no difference between beef and dairy cattle. As shown in Table 15, there was no significant difference in embryo production between 75, 112 or 150 units. It was concluded that 75 units was the optimum dose rate.

EXAMPLE 10

This example is a dose-rate study for a batch of FSH-S having a FSH/LH ratio of approximately 1655.

The FSH-S was prepared in accordance with the procedure described in Example 3.

The results are shown in Table 16 below.

TABLE 16

| Dose Rate | N | Transferable Embryos Mean ± SD | Total Ova + Embryos Mean ± SD |
|---|---|---|---|
| 75 | 5 | 8.29 ± 7.2 | 12.14 ± 8.41 |
| 112 | 5 | 2 ± 1.29 | 8 ± 8.33 |
| 150 | 5 | 1 ± 1.22 | 4.2 ± 4.92 |

This example demonstrates that a dose of 75 units of FSH-S gives optimum results in terms of both transferable embryos and total embryos and corroborates the results of Example 9.

EXAMPLE 11

This example demonstrates a study investigating dose and regimen effects of a FSH-W preparation having an FSH/LH ratio of 30,000. The FSH-W preparation was produced in accordance with the procedure described in Example 1. In this experiment, 120 cows were used in a 3×2 factorial design to test the effects of dose rate of FSH-W and treatment regimen on embryo production. The dose rates used were 2.7, 5.4, and 10.8 units (NIAMD-OFSH-13). The dose was administered in eight equal injections 12 hours apart (level) or 19, 14, 10 and 7% of total dose twice a day for four days (descending).

The results are shown in Table 17 below.

TABLE 17

| | | Dose mg FSH (5.4 mg = 75 units) | | | |
|---|---|---|---|---|---|
| | Regimen | 2.7 | 5.4 | 10.8 | Total |
| # Good Embryos Collected | level | 4.1 | 5.7 | 3.4 | 4.7 |
| | descending | 4.2 | 6.3 | 1.8 | 4.4 |
| | Total | 4.2 | 6.0 | 2.6 | |
| Total Embryos Collected | level | 6.9 | 10.5 | 9.1 | 9.0 |
| | descending | 6.8 | 12.7 | 13.4 | 10.5 |
| | Total | 6.8 | 11.4 | 11.5 | |
| % Good Embryos Collected | level | 59.3 | 59.3 | 23.9 | 53.2 |
| | descending | 66.8 | 48.7 | 18.8 | 48.5 |
| | Total | 63.4 | 54.6 | 21.3 | |
| # Fertilized | level | 5.8 | 7.9 | 6.1 | 6.9 |
| | descending | 5.6 | 10.2 | 3.4 | 6.7 |
| | Total | 5.7 | 8.9 | 4.5 | |
| % Fertilized | level | 78.8 | 79.4 | 41.6 | 72.6 |
| | descending | 85.7 | 75.3 | 27.5 | 67.3 |
| | Total | 82.7 | 77.6 | 32.9 | |
| # Degenerate Embryos | level | 1.4 | 2.0 | 1.9 | 1.8 |
| | descending | 1.5 | 3.6 | 1.6 | 2.3 |
| | Total | 1.5 | 2.7 | 1.7 | |
| % Degenerate Embryos Collected | level | 15.0 | 18.1 | 11.1 | 15.9 |
| | descending | 18.8 | 23.0 | 7.7 | 17.5 |
| | Total | 17.1 | 20.2 | 9.0 | |

The study demonstrated that level and descending dose regimes produced approximately equal results. The study also demonstrated there is a significant dose effect with respect to the following criteria: number of good embryos collected, total embryos collected, number fertilized and % fertilized. Finally, the study demonstrated there was not a significant dose effect with respect to the following criteria: number of degenerate embryos and % degenerate embryos.

EXAMPLE 12

This study was a direct comparison of cows treated with FSH-P having an FSH/LH ratio of 114 and cows treated with FSH-S having an FSH/LH ratio of 504.

The FSH-S used in this study was prepared in accordance with the procedure described in Example 3.

The results of this study are found in Table 18 below.

TABLE 18

| | FSH-P | FSH-S |
|---|---|---|
| N | 10 | 10 |
| # Good embryos | 0.69 | 5.80 |
| Total embryos | 7.60 | 8.70 |
| % Good embryos | 9.08 | 66.67 |

This study indicated that significantly better results in terms of number of good embryos and percent good embryos are achieved when cows are treated with FSH-S rather than FSH-P.

Super ovulation is used in many species of mammals using the same drug for a number of husbandry practices. Superovulation for embryo collection and transfer is used in sheep, cattle, swine, goats, horses, and many zoo mammals. Superovulation for production of multiple ovia which are allowed to develop is used for twinning in cattle and sheep and for out of season breeding in sheep. The physiological processes are the same and the invention works for multiple species of mammals in the same way as it does in cattle.

INTERSPECIES EFFECTS

The invention being universal for mammals in superovulation success, each species of FSH would work in another species. The following data using equine, ovine and porcine FSH in cows is shown in the following table, Table 19. It shows that FSH of three species (equine, ovine and porcine) is effective in producing superovulation in a fourth species (bovine).

TABLE 19

| Species | # Cows | # Transferable embryos | # Total embryos |
|---|---|---|---|
| Equine | 158 | 4.67 | 5.76 ± 6.29 |
| Ovine | 82 | 4.74 | 5.96 ± 5.84 |
| Porcine | 972 | 5.27 | 9.48 ± 8.49 |

OUT OF SEASON BREEDING IN SHEEP

Sheep are seasonal breeders which is a disadvantage in fat lamb production because it produces seasonal supplies. It is advantageous to produce lambs at other times of the year. These out of season lambs can only be produced if the ewes can be induced to breed out of season. The physiological processes involved in induction of estrus out of season are the same as those used in superovulation. Thus an experiment was designed to compare the use of FSH with a low LH content (FSH/LH>1000, SUPER-OV) with regular FSH-P (FSH/LH<500). The experiment was performed in New Zealand by officers of Waitaki International and supervised by officers of the Ministry of Agriculture and Fisheries. The aim in out of season breeding is to produce two ovulations per ewe. This is a distinction from superovulation when ovulation rate is maximized and the embryos are harvested. In out of season breeding the ewes are mated with rams and the embryos develop in the ewe without harvesting allowing for normal gestation of the embryo.

Thirty-eight ewes aged about five years were treated at random with either 2.5 units FSH (SUPER-OV, FSH/LH>1000) or 2.5 units FSH-P (Burns Biotec Omaha Nebr.)(FSH/LH<500). The ewes were pretreated with vaginal sponges containing a progestogen (The Upjohn Co., Kalamazoo, Mich.). The sponges were withdrawn four days after FSH treatment and the ewes slaughtered four days later. The total ovulations on both ovaries were counted.

FSH produced 1.525±0.6 ovulations, significantly more than the 0.1054±0.3 ovulations produced by FSH-P (P<0.001 by the TTest). A listing of the data and the TTest is presented in Table 20.

An FSH preparation with low levels of LH (SUPER-OV FSH/LH>1000) is a superior drug for out of season breeding of sheep to regular FSH-P with a high level of LH (FSH/LH<500).

TABLE 20
COMPARISON SUPER-OV WITH FSH-P
MARCH, 1987, DOSE 2.5 UNITS
Variable Under Analysis - # OVULATIONS
Variable used to Group Cases - TREATMENT

| FSH-P | |
|---|---|
| Number of cases = | 19 |
| Mean = | 0.1053 |
| Variance = | 0.0994 |
| Standard deviation = | 0.3153 |
| Standard error of the mean = | 0.0723 |
| SUPER-OV | |
| Number of cases = | 19 |
| Mean = | 1.5263 |
| Variance = | 0.3743 |
| Standard deviation = | 0.6118 |
| Standard error of the mean = | 0.1404 |
| T-Test statistics | |
| Difference (Mean X − Mean Y) = | −1.4211 |
| Standard error of the difference = | 0.1579 |
| t - statistic = | 9.0000 |
| Degrees of freedom = | 36 |
| Probability of t (One tailed test) = | 0.0000 |
| Probability of t (Two tailed test) = | 0.0000 |

TABLE 21
COMPARISON SUPER-OV WITH FSH-P
MARCH 1987, DOSE 2.5 UNITS

| TREATMENT | # OVULATIONS | DATE | DOSE (UNITS) |
|---|---|---|---|
| FSH-P | 0 | MAR87 | 2.5 |
| FSH-P | 0 | MAR87 | 2.5 |
| FSH-P | 1 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 1 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| FSH-P | 0 | MAR87 | 2.5 |
| SUPER-OV | 2 | MAR87 | 2.5 |
| SUPER-OV | 1 | MAR87 | 2.5 |
| SUPER-OV | 2 | MAR87 | 2.5 |
| SUPER-OV | 1 | MAR87 | 2.5 |
| SUPER-OV | 1 | MAR87 | 2.5 |
| SUPER-OV | 2 | MAR87 | 2.5 |
| SUPER-OV | 2 | MAR87 | 2.5 |
| SUPER-OV | 1 | MAR87 | 2.5 |
| SUPER-OV | 1 | MAR87 | 2.5 |
| SUPER-OV | 1 | MAR87 | 2.5 |
| SUPER-OV | 2 | MAR87 | 2.5 |
| SUPER-OV | 1 | MAR87 | 2.5 |

TABLE 21-continued
COMPARISON SUPER-OV WITH FSH-P
MARCH 1987, DOSE 2.5 UNITS

| TREATMENT | # OVULATIONS | DATE | DOSE (UNITS) |
|---|---|---|---|
| SUPER-OV | 3 | MAR87 | 2.5 |
| SUPER-OV | 2 | MAR87 | 2.5 |
| SUPER-OV | 1 | MAR87 | 2.5 |
| SUPER-OV | 2 | MAR87 | 2.5 |
| SUPER-OV | 2 | MAR87 | 2.5 |
| SUPER-OV | 1 | MAR87 | 2.5 |

SUPEROVULATION IN GOATS

In November, 1987, 24 goats were superovulated with either 30 units SUPER-OV or 30 units FSH-P (Schering Corporation, Kenilworth N.J.). The SUPER-OV had an FSH/LH ratio>1000 and the FSH-P<500. The goats were pretreated with progesterone and treated for four days with one of the FSH preparations. They were bred when they came in estrus and the embryos recovered nonsurgically six days after breeding. The recovered embryos were counted and classified as transferable (viable) or nontransferable.

SUPER-OV produced significantly more transferable embryos than the FSH-P. (8.7±1.9 vs. 5.7±3.6, P=0.227). There was no difference in the total embryos collected (9.2±2.1 vs. 7.8±3.9). The response from FSH-P was more variable than from SUPER-OV.

TABLE 22
SUPEROVULATION IN GOATS, WEST TEXAS
COMPARISON FSH-P AND SUPER-OV

| Subject | TREATMENT | DATE | DOSE (UNITS) | TRANSFERABLE EMBRYOS | TOTAL EMBRYOS |
|---|---|---|---|---|---|
| 1 | FSH-P | NOV87 | 30 | 6 | 14 |
| 2 | FSH-P | NOV87 | 30 | 2 | 3 |
| 3 | FSH-P | NOV87 | 30 | 6 | 6 |
| 4 | FSH-P | NOV87 | 30 | 7 | 8 |
| 5 | FSH-P | NOV87 | 30 | 1 | 3 |
| 6 | FSH-P | NOV87 | 30 | 5 | 6 |
| 7 | FSH-P | NOV87 | 30 | 8 | 10 |
| 8 | FSH-P | NOV87 | 30 | 12 | 12 |
| 9 | FSH-P | NOV87 | 30 | 0 | 2 |
| 10 | FSH-P | NOV87 | 30 | 6 | 7 |
| 11 | FSH-P | NOV87 | 30 | 5 | 10 |
| 12 | FSH-P | NOV87 | 30 | 11 | 12 |
| 13 | SUPER | NOV87 | 30 | 9 | 9 |
| 14 | SUPER | NOV87 | 30 | 8 | 10 |
| 15 | SUPER | NOV87 | 30 | 9 | 9 |
| 16 | SUPER | NOV87 | 30 | 9 | 9 |
| 17 | SUPER | NOV87 | 30 | 5 | 6 |
| 18 | SUPER | NOV87 | 30 | 7 | 7 |
| 19 | SUPER | NOV87 | 30 | 7 | 8 |
| 20 | SUPER | NOV87 | 30 | 9 | 9 |
| 21 | SUPER | NOV87 | 30 | 9 | 10 |
| 22 | SUPER | NOV87 | 30 | 12 | 12 |
| 23 | SUPER | NOV87 | 30 | 12 | 14 |
| 24 | SUPER | NOV87 | 30 | 8 | 8 |

TABLE 23
SUPEROVULATION IN GOATS, WEST TEXAS
COMPARISON FSH-P AND SUPER-OV
Variable under analysis - TOTAL EMBRYOS
Variable used to group cases - TREATMENT

| Group 1 FSH-P | |
|---|---|
| Number of cases = | 12 |
| Mean = | 7.7500 |
| Variance = | 15.4773 |
| Standard deviation = | 3.9341 |
| Standard error of the mean = | −1.1357 |
| Group 2 SUPER | |

TABLE 23-continued
SUPEROVULATION IN GOATS, WEST TEXAS
COMPARISON FSH-P AND SUPER-OV
Variable under analysis - TOTAL EMBRYOS
Variable used to group cases - TREATMENT

| | |
|---|---|
| Number of cases = | 12 |
| Mean = | 9.2500 |
| Variance = | 4.5682 |
| Standard deviation = | 2.1373 |
| Standard error of the mean = | 0.6170 |
| T-Test statistics | |
| Difference (Mean X − Mean Y) = | −1.5000 |
| Standard error of the difference = | 1.2925 |
| t - statistic = | 1.1606 |
| Degrees of freedom = | 22 |
| Probability of t (One tailed test) = | 0.1291 |
| Probability of t (Two tailed test) = | 0.2583 |

TABLE 24
SUPEROVULATION IN GOATS, WEST TEXAS
COMPARISON FSH-P AND SUPER-OV
Variable under analysis - TRANSFERABLE EMBRYOS
Variable used to group cases - TREATMENT

| | |
|---|---|
| Group 1 FSH-P | |
| Number of cases = | 12 |
| Mean = | 5.7500 |
| Variance = | 13.1136 |
| Standard deviation = | 3.6213 |
| Standard error of the mean = | 1.0454 |
| Group 2 SUPER | |
| Number of cases = | 12 |
| Mean = | 8.6667 |
| Variance = | 3.8788 |
| Standard deviation = | 1.9695 |
| Standard error of the mean = | 0.5685 |
| T-Test statistics | |
| Difference (Mean X − Mean Y) = | −2.9167 |
| Standard error of the difference = | 1.1900 |
| t - statistic = | 2.4510 |
| Degrees of freedom = | 22 |
| Probability of t (One tailed test) = | 0.0113 |
| Probability of t (Two tailed test) = | 0.0227 |

Food and Drug Administration regulations require that any multidose injectable use a preservative for the prevention of bacterial contamination of the multidose vial. On page 1491 of the U.S.P. XXI (Pharmaceutic Ingredients/Reference Tables) as listed by categories under the heading of Antimicrobial Preservative is listed Thymol along with other preservative materials. Thymol was found to be one in the list of the preservatives that does not damage glycoprotein hormones. In order to prove that Thymol can be used with the superovulation compound of the present invention as a preservative, it was established that 0.1% weight of Thymol does not harm FSH. A phosphate buffered saline was used as the diluent but other solutions such as normal saline would be safe to use. U.S.P. XXI, NF XVI Antimicrobial Preservative effectiveness tests were completed utilizing two levels of Thymol (0.08% and 0.04% by weight) against superovulation composition with diluent. Thymol at the 0.08% by weight was effective against all the test organisms and the 0.04% by weight was effective against four out of five.

Preservatives are substances added to dosage forms to protect them from microbial contamination. They are required to be added to multidose vials. Of the 24 antimicrobial preservatives listed on Page 1491 of U.S.P. XX 1, and U.S.P. and NF Pharmaceutical Ingredients, Thymol (5-methyl-2(1-methylethyl) phenol) was found to be compatible with FSH. Thymol is only slightly soluble in water, e.g., at 19° C. 1.3 g/liter and at 100° C. 1.6 gm/liter. Thus a useful working solution at room temperature is a 1% solution. It was therefore decided to test the compatibility of 1% Thymol in phosphate buffered saline on the activity of FSH over a period of four days, the recommended life of a multidose vial of SUPER-OV solution. SUPER-OV is a follicle stimulating hormone preparation that is used in inducing superovulation in mammals prior to estrus induction and subsequent insemination, embryo collection and transfer.

The purpose of this study was to evaluate the effects of 1% Thymol on the integrity of the biological activity of FSH when used in SUPER-OV DILUENT is used to dissolve SUPER-OV for use in divided doses over a four day period. The objective was to define the FSH activity of SUPER-OV after being in a solution of PBS or PBS and 1% Thymol for four days. PBS was made up to make a solution containing Sodium chloride 8%, Potassium chloride 0.02%, Potassium phosphate 0.02% and Sodium phosphate 0.102%. One vial each containing 75 units of FSH were used.

The experiment was started on Wednesday = $t_0$ ended on the following Sunday = $t_4$
One vial of FSH containing 75 units was dissolved in 6 ml PBS (12 units/ml). Two samples of 2.5 ml were taken and to each another 2.5 ml of PBS was added. To one subsample was added 60 lambda Thymol in Ethanol.

The ninth dilution of the $A_0$ 0 day, $A_t$ 4 day, $A_t$ 0 day and $A_t$ 4 day samples were assayed by the radioligand assay (Bousfield & Ward, 1984).

STATISTICS

The i.d.$_{50}$ plus or minus the standard deviation in uUnits/tube will be calculated for each parameter for the logistic $$F(x) = D + \frac{A - D}{1 + (X/C)^B}$$

where
- A = cpm at zero dose (counts per minute), i.e. the binding response in the absence of added unlabeled hormone.
- B = slope factor of the response curve.
- C = i.d.$_{50}$. The dose which displaces 50% of the specifically bound cpm (i.d.$_{50}$).
- D = cpm at infinite dose, i.e. the binding in the presence of an infinite dose of unlabeled ligand.
- X = dose of unlabelled ligand.
- F(x) = the binding response at a given dose of X (cpm).

This equation is utilized along with a program Curve fit routine (Newton Gauss best for analysis approach) for the analysis of the radioreceptor dose response curve. The Percent Total Specific Binding was plotted against Log Dose (mU/tube) for each FSH sample with and without Thymol preservative comparing the FSH standard used in the assay, the 0 and the 4 day result. The null hypothesis is that each of these curves will be the same.

Each 5 ml sample was further subdivided into two 2.5 ml samples, one to serve as the $t_0$ sample and the other as the $t_4$ sample. The following flow diagram represents this procedure.

FLOW DIAGRAM

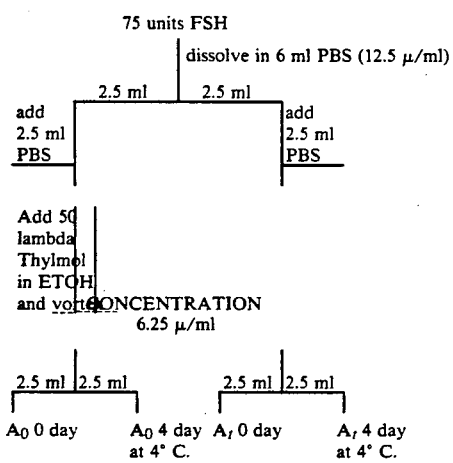

The 0 day samples were frozen immediately, and the 4 day samples after 4 days at 4° C.

At the time of assay the samples were thawed, diluted 1/10 with RLA buffer and the following serial dilutions made:

| Serial Dilution # | Concentration | × 50 lambda = Dose |
|---|---|---|
| 1 | 0.635 u/ml | 0.031 |
| 2 | 0.31 | 0.016 |
| 3 | 0.16 | 0.008 |
| 4 | 0.08 | 0.004 |
| 5 | 0.04 | 0.002 |
| 6 | 0.02 | 0.001 |
| 7 | 0.01 | 0.0005 |
| 8 | 0.005 | 0.00025 |
| 9 | 0.0025 | 0.00013 |

The treatments effects were compared, and the null hypothesis tested using the T-Test for matched pairs.

The FSH activity (units of NIH-FSH-s1/mg) for 4 treatments in 3 lots of SUPER-OV are listed in Table 25.

TABLE 25
FSH ACTIVITY AFTER DISSOLVING IN PBS AND PBS + 1% THYMOL

| Lot # | PBS Day 0 | PBS Day 4 | THYMOL Day 0 | THYMOL Day 4 |
|---|---|---|---|---|
| 603 | 0.85 | 0.61 | 0.53 | 0.67 |
| 700 | 0.94 | 1.37 | 1.30 | 0.84 |
| 706 | 0.58 | 0.65 | 0.53 | 0.53 |

TTests for matched pairs were conducted to compare Thymol day 0 vs. Thymol Day 4 (P=0.615 for null hypothesis Table 26), PBS day 0 vs. PBS day 4 (P=0.694, Table 27), 0 days vs. 4 days (P=0.938, Table 28) and PBS vs. Thymol (P=0.534, Table 29).

The percent total specific binding has been plotted against log dose for each FSH batch in PBS with and without Thymol comparing 0 days, 4 days and the NIH-FSH-S8 standard (FIGS. 2 to 6). The curves are nearly identical in each case indicating that there has been no change in FSH activity by putting it in PBS solution with and without 1% Thymol.

PBS or PBS containing 1% Thymol does not effect the FSH activity of SUPER-OV over a four day period making 1% Thymol a potential preservative for use in SUPER-OV DILUENT.

TABLE 26
TTEST COMPARING FSH POTENCY IN THYMOL AT 0 AND 4 DAYS

| THYMOL 0 TIME | |
|---|---|
| Mean = | 0.7867 |
| Variance = | 0.1976 |
| Standard deviation = | 0.4446 |
| Standard error of the mean = | 0.3144 |
| THYMOL 4 DAYS | |
| Mean = | 0.6800 |
| Variance = | 0.0241 |
| Standard deviation = | 0.1552 |
| Standard error of the mean = | 0.1098 |
| T-Test statistics | |
| Difference (Mean X − Mean Y) = | 0.1070 |
| Standard error of the difference = | 0.1812 |
| t - statistic = | 0.5886 |
| Degrees of freedom = | 2 |
| Probability of t (One tailed test) = | 0.3074 |
| Probability of t (Two tailed test) = | 0.6148 |

TABLE 27
TTEST COMPARING FSH POTENCY IN PBS AT 0 AND 4 DAYS

| PBS 0 TIME | |
|---|---|
| Mean = | 0.7900 |
| Variance = | 0.0351 |
| Standard Deviation = | 0.1873 |
| Standard error of the mean = | 0.1325 |
| PBS 4 DAYS | |
| Mean = | 0.8767 |
| Variance = | 0.1829 |
| Standard deviation = | 0.4277 |
| Standard error of the mean = | 0.3024 |
| T-Test statistics | |
| Difference (Mean X − Mean Y) = | 0.0870 |
| Standard error of the difference = | 0.1936 |
| t - statistic = | 0.4477 |
| Degrees of freedom = | 2 |
| Probability of t (One tailed test) = | 0.3472 |
| Probability of t (Two tailed test) = | 0.6943 |

TABLE 28
TTEST COMPARING FSH POTENCY AT 0 AND 4 DAYS

| ZERODAYS | |
|---|---|
| Mean = | 0.7883 |
| Variance = | 0.0931 |
| Standard deviation = | 0.3051 |
| Standard error of the mean = | 0.1365 |
| FOURDAYS | |
| Mean = | 0.7783 |
| Variance = | 0.0944 |
| Standard deviation = | 0.3073 |
| Standard error of the mean = | 0.1374 |
| T-Test statistics | |
| Difference (Mean X − Mean Y) = | 0.0100 |
| Standard error of the difference = | 0.1262 |
| t - statistic = | 0.0792 |
| Degrees of freedom = | 5 |
| Probability of t (One tailed test) = | 0.4690 |
| Probability of t (Two tailed test) = | 0.9361 |

TABLE 29
TTEST COMPARING FSH POTENCY IN PBS AND THYMOL

| PBS | |
|---|---|
| Mean = | 0.8333 |
| Variance = | 0.0895 |
| Standard deviation = | 0.2991 |

TABLE 29-continued

TTEST COMPARING FSH POTENCY
IN PBS AND THYMOL

| | |
|---|---|
| Standard error of the mean = | 0.1338 |
| THYMOL | |
| Mean = | 0.7333 |
| Variance = | 0.0921 |
| Standard deviation = | 0.3035 |
| Standard error of the mean = | 0.1357 |
| T-Test statistics | |
| Difference (Mean X − Mean Y) = | 0.1000 |
| Standard error of the difference = | 0.1256 |
| t statistic = | 0.7961 |
| Degrees of freedom = | 5 |
| Probability of t (One tailed test) = | 0.2668 |
| Probability of t (Two tailed test) = | 0.5337 |

While the present invention has been described in detail and with reference to specific examples thereof, it will be apparent to one skilled in the art that various changes and modifications can be made therein without departing from the spirit and scope thereof.

What is claimed is:

1. A composition of matter for producing superovulation in a domestic animal selected from the group consisting of sheep, goats, swine, horses and cattle comprising:

an effective amount of follicle stimulation hormone and lutenizing hormone, wherein the ratio of follicle stimulation hormone to lutenizing hormone is in a range of from about 500 to about 30,000 to 1, and a pharmaceutical solution of saline or phosphate buffered saline and an effective amount of an antimicrobial preservative comprising 5-methyl-2(1-methylethy)phenol.

2. The composition of matter of claim 1 wherein the ratio of follicle stimulation hormone to lutenizing hormone is in the range of from about 1,000 to about 23,000:1.

3. The composition of claim 1, wherein said preservative 5-methyl-2(1-methylethyl)phenol comprises at least 0.04% by weight of the pharmaceutical solution.

4. The composition of claim 1, wherein said preservative 5-methyl-2(1-methylethyl)phenol comprises about 0.05 to about 0.1% by weight of the pharmaceutical solution.

5. A composition of matter for producing superovulation in goats comprising:

an effective amount of follicle stimulation hormone and luteinizing hormone, wherein the ratio of follicle stimulation hormone to luteinizing hormone is in a range of from about 500 to about 30,000 to 1.

6. A composition of matter for producing superovulation in swine comprising:

an effective amount of follicle stimulation hormone and luteinizing hormone, wherein the ratio of follicle stimulation hormone to luteinizing hormone is in a range of from about 500 to about 30,000 to 1.

7. A composition of matter for producing superovulation in sheep comprising:

an effective amount of follicle stimulation hormone and luteinizing hormone, wherein the ratio of follicle stimulation hormone to luteinizing hormone is in a range of from about 500 to about 30,000 to 1.

8. A composition of matter for producing superovulation in horses comprising:

an effective amount of follicle stimulation hormone and luteinizing hormone, wherein the ratio of follicle stimulation hormone to luteinizing hormone is in a range of from about 500 to about 30,000 to 1.

9. A method for producing superovulation in a domestic animal selected from the group consisting of sheep, goats, swine, horses and cattle comprising administering to said domestic animal a composition of an effective amount of follicle stimulating hormone and lutenizing hormone, wherein the ratio of follicle stimulating hormone to lutenizing hormone is in a range of from about 500 to about 30,000 to 1.

10. The method for producing superovulation in a domestic animal according to claim 9, wherein said composition is administered to the domestic animal by parenteral injection.

11. The method for producing superovulation in a domestic animal according to claim 10, wherein said composition is administered to the domestic animal in eight (8) equal doses at approximately twelve (12) hour intervals.

12. A method for achieving out of season breeding for a domestic animal selected from the group consisting of sheep, goats, swine, horses and cattle characterized as having breeding seasons comprising:

administering to the seasonal breeding domestic animal a composition of matter comprising an effective amount of follicle stimulating hormone and lutenizing hormone, wherein the ratio of follicle stimulating hormone to lutenizing hormone is in a ratio of from about 500 to about 30,000 to 1.

13. The method according to claim 12 wherein the domestic animal is selected from the group consisting of cattle, sheep, goats and horses.

* * * * *